United States Patent
Beaty et al.

(10) Patent No.: US 9,091,623 B2
(45) Date of Patent: Jul. 28, 2015

(54) SYSTEM TO DETERMINE PRODUCT CHARACTERISTICS, COUNTS, AND PER UNIT WEIGHT DETAILS

(71) Applicant: Satake USA, Inc., Stafford, TX (US)

(72) Inventors: William Keith Beaty, Webster, TX (US); Patric Carey Pike, Hopkins, MI (US); Calvin G. Gray, Richmond, VA (US)

(73) Assignee: Satake USA, Inc., Stafford, TX (US)

( * ) Notice: Subject to any disclaimer, the term of this patent is extended or adjusted under 35 U.S.C. 154(b) by 73 days.

(21) Appl. No.: 14/173,056

(22) Filed: Feb. 5, 2014

(65) Prior Publication Data
US 2014/0169629 A1   Jun. 19, 2014

Related U.S. Application Data

(63) Continuation-in-part of application No. 13/448,351, filed on Apr. 16, 2012, now Pat. No. 8,682,027, which is a continuation-in-part of application No. 12/706,028, filed on Feb. 16, 2010, now Pat. No. 8,175,372.

(60) Provisional application No. 61/152,930, filed on Feb. 16, 2009.

(51) Int. Cl.
*G01N 15/10* (2006.01)
*G06T 7/40* (2006.01)
(Continued)

(52) U.S. Cl.
CPC .............. *G01N 15/10* (2013.01); *G01N 33/02* (2013.01); *G06T 7/0004* (2013.01); *G06T 7/40* (2013.01);
(Continued)

(58) Field of Classification Search
CPC ....... G01N 33/02; G01N 15/10; G01N 21/85; G01N 23/12; G01N 2015/1062; G01N 2015/1043; G01N 2015/1081; G01N 2015/1486; G01N 2015/149; G01N 2021/8592; G01N 2033/0077; G01N 2223/643; G01N 2223/645; G06T 7/0004; G06T 7/40; G06T 5/30; G06T 2207/10024; G06T 2207/20036; G06T 2207/30108; G06T 2207/30128; G06T 2207/30242; G06K 9/4604
See application file for complete search history.

(56) References Cited

U.S. PATENT DOCUMENTS 4,125,828 A   11/1978   Resnick et al.
4,260,262 A   4/1981   Webster
(Continued)

OTHER PUBLICATIONS
Manav Seth, Notice of Allowance—U.S. Appl. No. 12/706,028, Jan. 9, 2012, 9 pages, United States Patent and Trademark Office, Alexandria, Virginia, United States.
(Continued)

*Primary Examiner* — Manav Seth
(74) *Attorney, Agent, or Firm* — Crain, Caton & James, P.C.; James E. Hudson, III

(57) ABSTRACT

A system for determining the characteristics of a volume of preferable small fungible products within an acceptable size range. The system differentiates among products even if in close contact to identify acceptable product. The system may store data for later review or for dispensing of product in real time. The system may include a scale to determine a sample's weight, a camera to image the sample, an imaging table to permit viewing of the sample, a processor to determine the number of products in the sample, and a processor to determine the density of desired product. The system may also determine product count-per-weight, product volume-per-weight, and/or product surface-area-per-weight. These determinations may be useful, including in determining product processing and packaging options.

12 Claims, 13 Drawing Sheets

(51) Int. Cl.
   *G01N 33/02* (2006.01)
   *G06T 7/00* (2006.01)
   *G01N 33/00* (2006.01)

(52) U.S. Cl.
   CPC .. *G01N 2033/0077* (2013.01); *G01N 2223/643* (2013.01); *G06K 2209/17* (2013.01); *G06K 2209/19* (2013.01); *G06T 2207/10024* (2013.01); *G06T 2207/20036* (2013.01); *G06T 2207/30242* (2013.01)

(56) References Cited

U.S. PATENT DOCUMENTS

| | | | |
|---|---|---|---|
| 4,448,680 A | | 5/1984 | Wilks et al. |
| 4,635,215 A | | 1/1987 | Friend |
| 4,713,781 A | | 12/1987 | Brizgis et al. |
| 4,793,706 A | | 12/1988 | Csillag et al. |
| 4,975,863 A | | 12/1990 | Sistler et al. |
| 5,321,764 A | | 6/1994 | Cullen et al. |
| 5,703,784 A | | 12/1997 | Pearson |
| 5,751,421 A | | 5/1998 | Wright et al. |
| 5,898,792 A | | 4/1999 | Oste et al. |
| 5,917,927 A | * | 6/1999 | Satake et al. ............ 382/110 |
| 6,078,635 A | | 6/2000 | DuBois |
| 6,100,526 A | | 8/2000 | Mayes |
| 6,186,194 B1 | | 2/2001 | Poupon |
| 6,418,180 B1 | | 7/2002 | Weiss |
| 6,438,259 B1 | | 8/2002 | Anderson et al. |
| 6,624,888 B2 | | 9/2003 | Panigrahi et al. |
| 6,630,672 B1 | | 10/2003 | Brotherton et al. |
| 6,635,840 B1 | | 10/2003 | Mailloux |
| 6,706,989 B2 | | 3/2004 | Hunter et al. |
| 6,845,326 B1 | | 1/2005 | Panigrahi et al. |
| 6,851,662 B2 | | 2/2005 | Panigrahi et al. |
| 7,218,775 B2 | | 5/2007 | Kokko et al. |
| 7,290,665 B2 | | 11/2007 | Hunter et al. |
| 8,175,327 B2 | | 5/2012 | Beaty et al. |
| 8,831,292 B2 | * | 9/2014 | Brueckner et al. ............ 382/110 |
| 2005/0060958 A1 | | 3/2005 | Harmon et al. |
| 2008/0009962 A1 | | 1/2008 | Hood et al. |
| 2008/0034652 A1 | | 2/2008 | Hunter et al. |
| 2008/0035532 A1 | | 2/2008 | Hunter et al. |
| 2008/0179226 A1 | | 7/2008 | Hunter et al. |
| 2008/0265141 A1 | | 10/2008 | Leuenberger et al. |
| 2009/0046890 A1 | | 2/2009 | Hausmann et al. |
| 2010/0002929 A1 | | 1/2010 | Sammak et al. |
| 2010/0208936 A1 | | 8/2010 | Beaty et al. |
| 2012/0218403 A1 | | 8/2012 | Beaty et al. |
| 2013/0021469 A1 | * | 1/2013 | Conrad et al. ............ 348/135 |

OTHER PUBLICATIONS

Nav Seth, Notice of Allowance—U.S. Appl. No. 13/448,351, Nov. 22, 2013, 11 pages, United States Patent and Trademark Office, Alexandria, Virginia, United States.

* cited by examiner

SYSTEM TO DETERMINE PRODUCT CHARACTERISTICS, COUNTS, AND PER UNIT WEIGHT DETAILS

CROSS-REFERENCE TO RELATED APPLICATIONS

This is a continuation-in-part of U.S. patent application Ser. No. 13/448,351, entitled System to determine product density, filed Apr. 16, 2012, and of U.S. patent application Ser. No. 12/706,028, entitled System to determine in near real-time product density in a continuous dispensing product flow, filed Feb. 16, 2010, issued as U.S. Pat. No. 8,175,327 on May 8, 2012, and, as a continuation-in-part thereof, claims the benefit of U.S. Provisional Patent Application No. 61/152,930 entitled "Seed count estimator" filed on Feb. 16, 2009 in the United States Patent and Trademark Office from which priority is claimed, and which are incorporated herein by reference.

STATEMENT REGARDING FEDERALLY SPONSORED RESEARCH OR DEVELOPMENT

Not Applicable.

BACKGROUND

1. Field

The present disclosure pertains to systems for providing details regarding a sample, including an approximate count of small fungible products, such as seeds and plastic pellets. More particularly the present disclosure relates to determining geometric characteristics, and potentially further the density, of the fungible products in a volume, potentially in an associated or parallel product flow so user can select optimum settings for further processing equipment or so the system or a separate connected system can dispense a close approximation of a specific quantity based on the volume calculation derived from product density rather than dispensing by estimated weight only or for assessment of product received. The user now has the ability to precisely set coating equipment or to vary the weight in order to achieve a very accurate piece count in a packaging operation.

2. Description of the Related Art

Processing operations for seeds provide a clear background for the present type of system. In traditional seed processing operations, the operator receives bulk deliveries of the desired seed, which include undesirable elements in each delivery; which may also include hulls, rocks, insects, plant matter, weed seeds, and pieces of desirable seeds. The operator utilizes various equipment to remove these undesirable constituents, leaving only whole desired seeds. This may include receiving, cleaning, treating, potentially storing, and packing seed for purchase, typically by weight. While purchase by actual number of seeds is desirable, due to variations in source and timing, in processing to remove undesirable constituents, the number of seeds per unit weight, the seed density, varies. Additionally, when seeds of differing suppliers are combined, the seeds received may vary in size and moisture content yielding much different densities from supplier to supplier. Due to these variations, operators have historically been unable to accurately deliver a specific number of seeds per package, where the package in question may range from fifty (50) pounds to ten thousand (10,000) pounds. This creates issues for purchasers, among others, who desire to purchase a certain quantity of seeds, typically enough for seeding of a particular area but not so much as to have leftover, and often thereafter unusable, seed. Leftover seed may be unusable because of storage issues, germination period, and, particularly with the rise of genetically-modified and patented seeds, most importantly legal permissions. Thus, inconsistent seed counts can create substantial issues, sometimes providing an insufficient or wasteful quantity of seeds when computed on the anticipated planting rate. When attempting to provide seeds based on quantity, operators have intentionally underestimated the number of seeds likely to be a particular weight bag so as to guarantee purchasers receive enough seed. This, however, results in waste as unnecessary, and therefore unusable, seed is provided to purchasers. Moreover, operators lose potential revenues on each sale solely to ensure sufficient seeds per sale. Regulatory authorities monitor the accuracy of the labeling on the seed packaging and the "count" or number of seeds per container must fall within mandated limits. In addition the processor may desire to purchase seeds by the count rather than weight. While not tested for this application the disclosure could provide utility in this and many other bulk product handling facilities.

Attempts to provide accurate seed counts have focused on providing a true count of seeds by processing each seed through a counter. One attempt at resolving this situation has provided for each single seed to be drawn past a photoelectric sensor and individually counted. In another attempt, a sampling of seeds is vibrated past a series of photodetector cells or seed counters and individually counted, and then weighed, to determine a theoretical mass for the desired seed count. Problematically, these systems require that each seed be actually counted, which results in substantial reduction in speed of processing and which does not adequately address the issue of broken seeds, and of distinguishing individual seeds which are larger than the standard size from clusters of seeds. In another attempt in the prior art, an image of uniformly-sized, and ideally uniformly-distributed, seeds on a horizontal surface is processed to determine average object size and extrapolated to determine an estimated total object count for the imaged seeds. Problematically, this system provides only a estimated count based on computer average size based on a single review and provides no means to limit the count being directed to a bag or other output. Moreover, the requirement of a uniform size of seeds can create issues as seed size may vary significantly. Unequal distribution, particularly due to clusters of seeds, skews the results.

Additionally, attempts to modify existing systems to include equipment to provide accurate seed counts have been economically unfeasible, requiring line retooling and capital investment and utilizing systems generating stale data. The current systems require, in some cases, as much as 30 minutes to determine the applicable density data. In such cases, by the time the density date is available, the density of the passing product may have substantially deviated from the determination, providing data of little utility.

Moreover, it is sometimes desirable to obtain, or retain, samples of smaller quantities for assessment. Such sampling generally requires small discrete samples.

Additionally, it would be beneficial to obtain and utilize characteristics, such as product size, surface area and volume, for uses such as process control and equipment selection.

Thus, there is a need in the art for a system for use in product processing operations that rapidly determines the density of products, which can do so by eliminating broken products from the count, counting the products within clusters, and counting products of varying sizes and which, when desired, may also be used to obtain a desired product count per bag with little waste. Ideally, there is a need for a system which may be integrated easily into existing operations and the current product handling systems without excessive line retooling and without substantial capital investment or which may be used for laboratory or testing assessments. There is also a need for a system which integrates with the current plant information and control systems along with the weigh-bagger to provide an accurate method for dispensing a weight that contains a very accurate number of objects (seeds), particularly one designed to work in-line and support high volume operations. There is also a need for a system which obtains and utilizes product geometry based on accurate images obtained. Moreover, there is a need for accurate, real-time seed count per pound data to improve package count accuracy and reduce give-away. Finally, there is a need for a platform which allows useful additional data to be collected regarding product geometry, density, and count-per-unit weight.

SUMMARY

The present disclosure therefore meets the above needs and overcomes one or more deficiencies in the prior art by a system that rapidly determines the density of products and, which may be used for assessment, or to obtain a desired product count per bag with little waste, and which can do so by eliminating broken products from the count, counting the products within clusters, and counting products of varying sizes. Moreover, the present disclosure provides a system which may be used in laboratory or test environments or which integrates easily into existing operations and the current product handling systems, thus reducing line retooling and reducing the total capital investment. The system may be integrated with the current plant information and control systems along with the weigh-bagger to provide an accurate method for dispensing a weight that contains a very accurate number of objects (seeds). Where integrated for production use, the system is designed to work in-line and support high volume operations. Thus, the disclosure provides systems and methods for determining the product density value of preferable small fungible products within an acceptable size range within an acceptable color range The system for determining the product density value of preferable small fungible products within an acceptable size range may comprise a weight scale, an imaging table, a camera, a counting processor, and a density processor. The weight scale may be adapted to determine a sample weight value indicative of the weight of a sample. The camera may be adapted to transmit at least one image, having at least two color ranges or having a specific color range, of said imaging table to the counting processor where the counting processor is adapted to identify each acceptable product in said sample within said acceptable size range and determine the number of acceptable products. The counting processor may be adapted to identify at least two counts within said number of said acceptable products according to two or more colors, to perform a morphological erosion on said at least one image of said products above said acceptable size range until all of said products above said acceptable size range appear separated or in predictable count clusters, and to determine the number of said separated products and the number of products in said predictable count clusters. The counting processing may further be adapted to combine the number of acceptable products within the sample and within the acceptable size range and the number of separated products to determine a sample count. The density processor is adapted to receive an input of the sample weight value and to determine product density value by dividing the sample count by the sample weight value.

Thus, the present disclosure includes a container which defines a sample of products, a framework, a scale, a processor, an imaging table, and an associated camera. The system may be connected to an automated bagger/scale, a display for a manually-operated bagger/scale, or to a plant computer system for bagging, quality control, or record keeping. The disclosure accurately weighs a sample of product with a high degree of precision, accurately counts the quantity of product in the sample, and determines the value of the product density of the associated and larger zone of the product flow. Determination of the value of the product density provides several benefits. Where a desired quantity is to be dispensed, once the product density value is known for a particular zone of product flow, the desired minimum weight necessary to obtain the desired product count from that zone may be determined and a bagger/scale controlled to obtain that minimum weight.

In operation, the method determines the product density value of preferable small fungible products within an acceptable size range and within an acceptable color range, by 1) obtaining a sample of mixed products; 2) determining a sample weight of said sample; 3) imaging said sample to produce at least one image having at least two color ranges; 4) processing said at least one image to identify and count the individual preferred small fungible products within said acceptable size range and within said acceptable color range, to identify areas of said image containing objects larger than the small preferred small fungible products within said acceptable size range and within said acceptable color range, and to retain only said areas of the at least one image containing objects larger than the preferred small fungible products within said acceptable size range and within said acceptable color range; 5) repeatedly processing said at least one image to morphologically erode said objects larger than the preferred small fungible products within said acceptable size range and within said acceptable color range, to identify the mean size of the eroded objects, determining an acceptable eroded object size about said mean size, processing said at least one image to identify and count the eroded objects within said acceptable size and within said acceptable color range, and to retain only said areas of the at least one image containing eroded objects larger than said acceptable size, until no eroded objects remain; 6) combining said count of the number of said individual preferred small fungible products and said count of the number of eroded objects within said acceptable size and within said acceptable color range to produce a sample count; 7) determining said product density value by dividing said sample count by said sample weight value; and 8) outputting said determination of product density value.

The disclosure describes capturing images or taking a picture of the sample in a two tone, black-and-white, or dichromatic image, counts products within a size range, and then uses a morphological process to identify and count products in clusters or products larger than the product range. The system allows the images to be saved in digital format to permit future retrieval for use in plant audits and historical validation of the material processes at any given time.

In another embodiment a color camera is used and the color of the product can also be assessed. Applications for this embodiment include the simultaneous counting of the seeds in a sample and the categorization of those seeds into two or more subgroups, such as off-color versus prime, or resistant versus refuge based on treatment coating color in refuge-in-bag seed packaging operations.

In a further embodiment, these images, generated at high resolution, may be used to determine, via calculation, geometric data for the individual objects in the process flow, which may then be used to address a wide range of needs in the processing of small fungible products, including on a per unit weight basis. An image from the imaging table may be used for calculation of geometric data. Because of the unique product presentation of the present invention the two dimensional image of three dimensional objects can be used to calculate parameters such as axis ratio, relative size or shape, etc., which are based on dimensions directly measured in the image and which may be applied to determine characteristics on per unit weight basis. The length and width (major and minor axes) of each object are easily measured with standard vision tools such as inner and outer circles, minimum bounding rectangle, etc. Other valuable discriminators can be derived by using the wide range of geometric properties that can be calculated from the objects isolated in the image during the basic function of calculating the seed count per unit of mass. Where the third dimension, the thickness, is estimated, additional valuable information can be extracted from the image.

For products such as corn with widely differing shapes it is necessary to make assumptions about the thickness of each object. Characterization studies allow the geometry of these products to be quantified. Corn kernels are typical separated by a mechanical screening process to divide the lot into kernels that are substantially flat and kernels that are substantially round. These two categories can be characterized separately. Moreover, characterization may include comparison of the size and shape of the product to the weight of the product. As the weight of a product is roughly proportional to the volume of a product, the weight of a product may be used to estimate the volume of a product and given the two dimensions known of the product, also to estimate the thickness of a product.

Because the product rests on a flat surface, each product takes on a uniform orientation, i.e. the most stable resting position based on the shape of the product. As the products are fed to the imaging stage and vibration is applied, they naturally settle so that the center of gravity is at its lowest point. The vertical dimension is therefore equal to or less than the other dimensions of the product, a detail which further improves accuracy of surface area and volume determination. This uniform orientation is present to the camera, which is captured as an image. This benefit would not be available for product present to an imaging system associated with a free fall system, as product is not oriented along a common axis, frustrating any attempt to measure the major axis and the length of the two axes at right angles to the major axis.

The geometric characteristics of fungible objects can provide important information for process control and for processing. For example, processing may include the application of surface treatments to products such as seeds. This surface treatment is typically applied based on product density, such as the average number of pieces per unit of mass. Since the treatment adheres to the surface of each piece, it is valuable to know the surface area of the pieces in the process flow. It is important to determine not only the average surface area, but also the range of surface area from the smallest piece to the largest piece in the lot. Since the surface treatment will adhere in proportion to the surface area, smaller objects may be under treated and larger objects may be over treated. Surface area variability within the sample is an important process measure.

Another important application of the geometric data from the high resolution image provided by the present invention is in the setup of mechanical size grading (screen separator) equipment in the processing line. Geometric data from images of pre-production samples can provide reliable modeling information to predict the accept stream and discard stream from the grading equipment when that lot goes into production. In the example of soybeans, the present invention can provide dimensions for the length width and thickness of every object in the sample. From these dimensions the system can accurately calculate the volume of every object in the sample. Totaling the volume of all objects in the sample and apportioning the mass of the sample in proportion to the volume of each object provides an accurate estimate of the mass of each object in the sample. Knowing the dimensions and mass of each object, the system can predict the results of the grading operation and the screen selection can be determined to optimize the balance between yield loss and size uniformity for the lot. The system can also be used to evaluate the performance of the size grading equipment and the processing equipment removing oblong and split objects.

A third benefit from correctly assessing the size/shape variability is correctly matching seed lots to the different types of planting equipment in use in the agricultural industry. It is important in row crops such as corn and soybeans that seeds be precisely spaced and that no gaps occur during the planting process. Different types of planters are optimized for specific seed shapes, and consistency of shape and size is an important measure of seed quality.

Thus, having an accurate count of product per unit weight, product may be directed to a packaging bin where an average count of product per unit weight can be used to set bag weight for accurate packaging. Alternatively, another embodiment of the present disclosure may placed directly before packaging to dynamically set bag weight and fully optimize the package weight. Additionally, product having completed a cleaning process and assessed according to the present disclosure may be directed to treatment application (surface application of a chemical slurry), where the real-time geometric data, particularly surface area per pound, can be used to set treatment rates before packaging, which may include further application of the present disclosure as the count per pound at that point will be different because of the weight added in the chemical slurry. The count of product per unit weight before treating, plus an allowance for the added weight of the treatment, can still be used to set bag weight using the average for the product in the treated packaging bin, which may include further application of the present disclosure in the process directly ahead of the packaging operation to dynamically set bag weight and fully optimize the package weight.

The geometric data can be used to evaluate the performance of the screening/separating setup in the seed cleaning operation.

Additionally, this geometric and weight data may be used in off-line operations to characterize the sample so that the correct screening/separating setup is specified in advance so that the processing line can be set up optimally.

Moreover, in the variety development process, documenting geometric properties for each generation can help to predict how a new variety will process when it goes into production.

In yet another embodiment, the present disclosure includes a scale, a processor, an imaging table, and an associated camera for laboratory application where samples are fed manually by an operator. The system can be packaged as a bench top unit to provide all of the rapid analysis and data connectivity advantages of the on line unit, but as a lab instrument.

Additional aspects, advantages, and embodiments of the disclosure will become apparent to those skilled in the art from the following description of the various embodiments and related drawings.

BRIEF DESCRIPTION OF THE DRAWINGS

So that the manner in which the described features, advantages, and objects of the disclosure, as well as others which will become apparent, are attained and can be understood in detail; more particular description of the disclosure briefly summarized above may be had by referring to the embodiments thereof that are illustrated in the drawings, which drawings form a part of this specification. It is to be noted, however, that the appended drawings illustrate only typical preferred embodiments of the disclosure and are therefore not to be considered limiting of its scope as the disclosure may admit to other equally effective embodiments.

In the drawings.

DESCRIPTION OF THE PREFERRED EMBODIMENT

Figure 1:
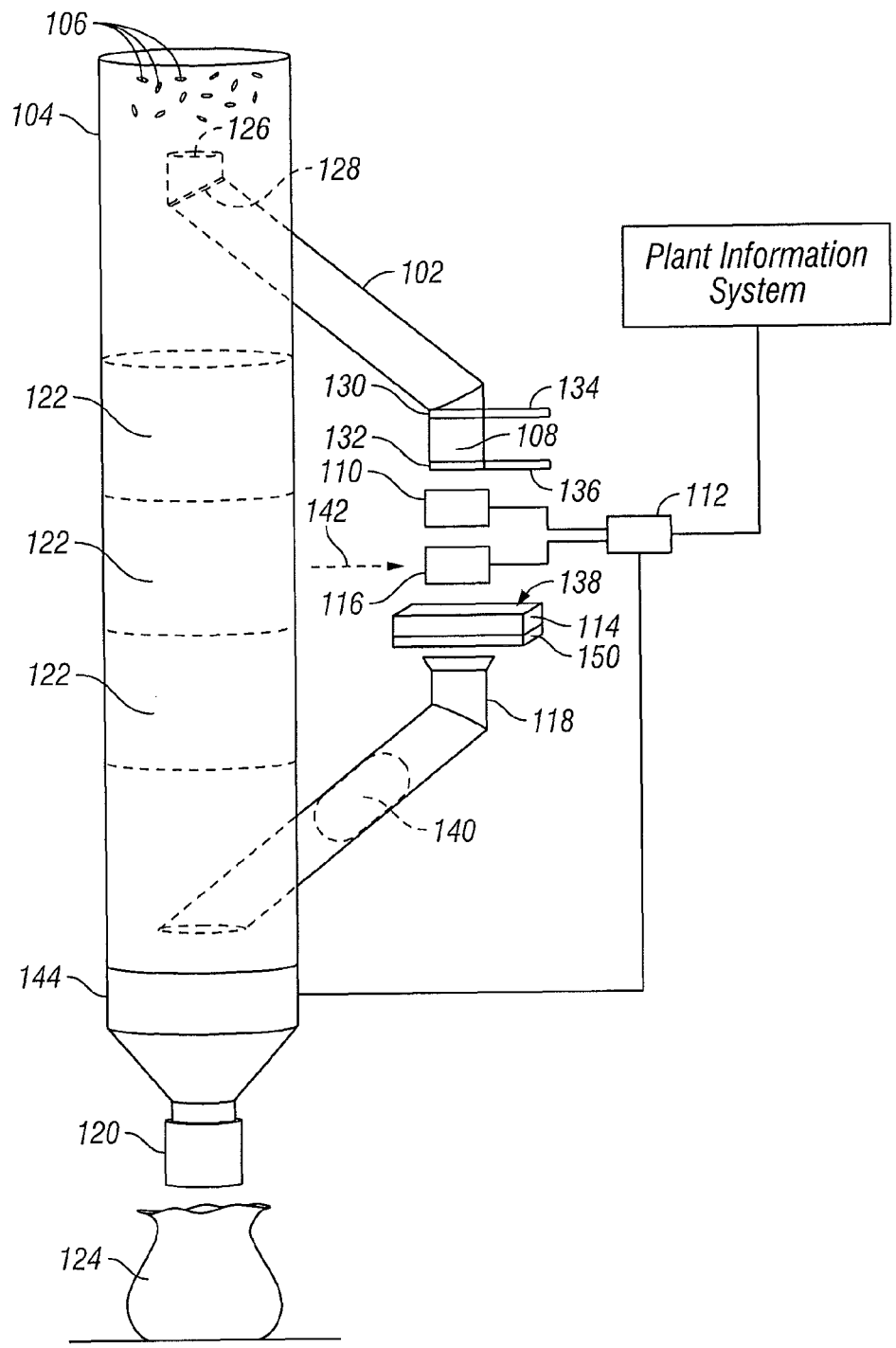
FIG. 1 is an illustration of one embodiment of the present disclosure in connection with an existing product bin, bagger/scale, and bag.

Referring to FIG. 1, the disclosure provides systems and methods for determining the product density value of preferable small fungible products within an acceptable size range within an acceptable color range. In particular, the disclosure includes a system which includes a sample input piping 102 from a bin or piping 104 of products 106, such as selected preferable small fungible products and which may be a mixed flow further including undesirable contaminants, through which products 106 flow, a sampling volume 108, for defining a sample 140, a weight scale 110, a processor 112, an imaging table 114 and an associated camera 116. The system may include a sample output pipe 118, and may include or be associated with a bagger/scale 120. Operation of these components provides for successively sampling of each zone 122 in the bin 104 to determine the quantity of acceptable product per unit weight. While this data may be used for later historical review, it may be also be utilized with a bagger/scale 120 particularly to determine a desired weight of product for that zone equivalent to the desired product quantity, and to terminate operation of a bagger/scale 120 when the desired weight of the product 106 at the bagger/scale 120 is reached, thus adjusting the weight of the products 106 dispensed into each bag 124 containing the products 106 based on the associated zone 122. Such use may require a dedicated processor or a site-based computer network. If so used, the weight of the bags 124 of the products 106 dispensed by a bagger/scale 120 will vary over time and, dependent on source of the products 106 in that zone while the product count for each bag 124 will be roughly equivalent. This system therefore can compensate for variations among supplying entities where product supplies are subsequently piled atop one another.

Still referring to FIG. 1, the sample input piping 102, which may be a pipe, or a channel or other structure to communicate seeds, is in communication with the bin or piping 104. In one embodiment the sample input piping 102 penetrates through the side wall of the bin or piping 104 to the center of the sample input piping 102, where the sample input piping 102 terminates in an upward opening 126. Thus, as each zone 122 of the products 106 moves downward a representative sampling of the zone passes into the sample input piping 102, a flow diversion step 202 identified in FIG. 2. The sample input piping 102 has a first end and a second end, with the sample input piping 102 adapted for communication with the sample volume 108 at the second end of the sample input piping 102. The sample input piping 102 is also adapted for communication with the bin 104 of products 106, particularly where the products 106 are in one or more of said zones 122 in the bin 104. In such situations, the products 106 in each of the one or more of said zones 122 generally have nearly equivalent characteristics of size, weight and percentage of desired products. A gate 128 may be located at the upward opening 126 to further control the flow into the sample input piping 102 but may also be omitted. The sample input piping 102 is also in communication with a sampling volume 108 which may include a top gate 134 at its top side 130 and a bottom gate 136 at its bottom side 132, defining a sampling container. The sampling container has an internal volume, which, when full, defines the sample by defining the sampling volume 108. The sample input piping 102 must therefore have a sufficient sized opening to draw from a zone 122 of the bin or piping 104. The sample input piping 102 ideally operates on a gravity feed, downwardly descending as it passes out of the bin or piping 104. The sample input piping 102 may be in contact with or connected to an eccentric or vibratory motor or other vibration-inducing device, such as a vibratory feeder 150, which may be connected to the sample input piping 102 to ensure the products 106 do not bridge, or stack atop of or in the sample input piping 102.

Figure 2:
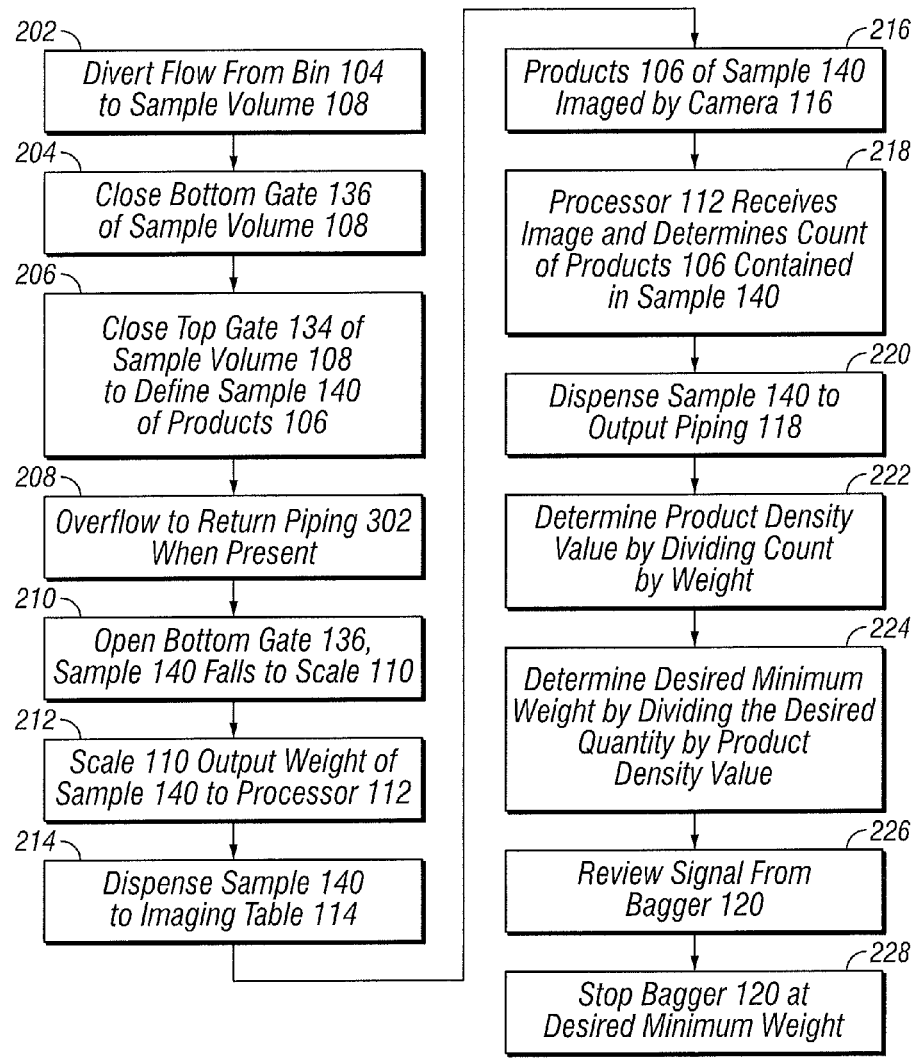
FIG. 2 is a flowchart of steps of the present disclosure for use with an existing product bin.

In operation, closing the bottom gate 136, step 204 of FIG. 2, defines the bottom of the sampling volume 108 and closing the top gate 134 prevents the addition of further products 106 into the sampling volume 108, and therefore defines the sample 140 when filled with products 106, particularly the volume of the sample 140. As can be appreciated, it is essential that the flow of the products 106 be metered to control the volume of the products 106 introduced to the present system as a sample 140. The top gate 134 may be closed, step 206 of FIG. 2, based on a pre-determined point in operation, which may by time, or a switch located in the sampling volume 108. The volume of the sample 140 may be defined by lengthening the sampling volume 108 or by increasing or decreasing the usable interior volume of the sampling volume 108, such as by inserts or interchangeable sampling volumes 108. The sample 140 may be collected at the time determined by a processor 112.

Figure 3:
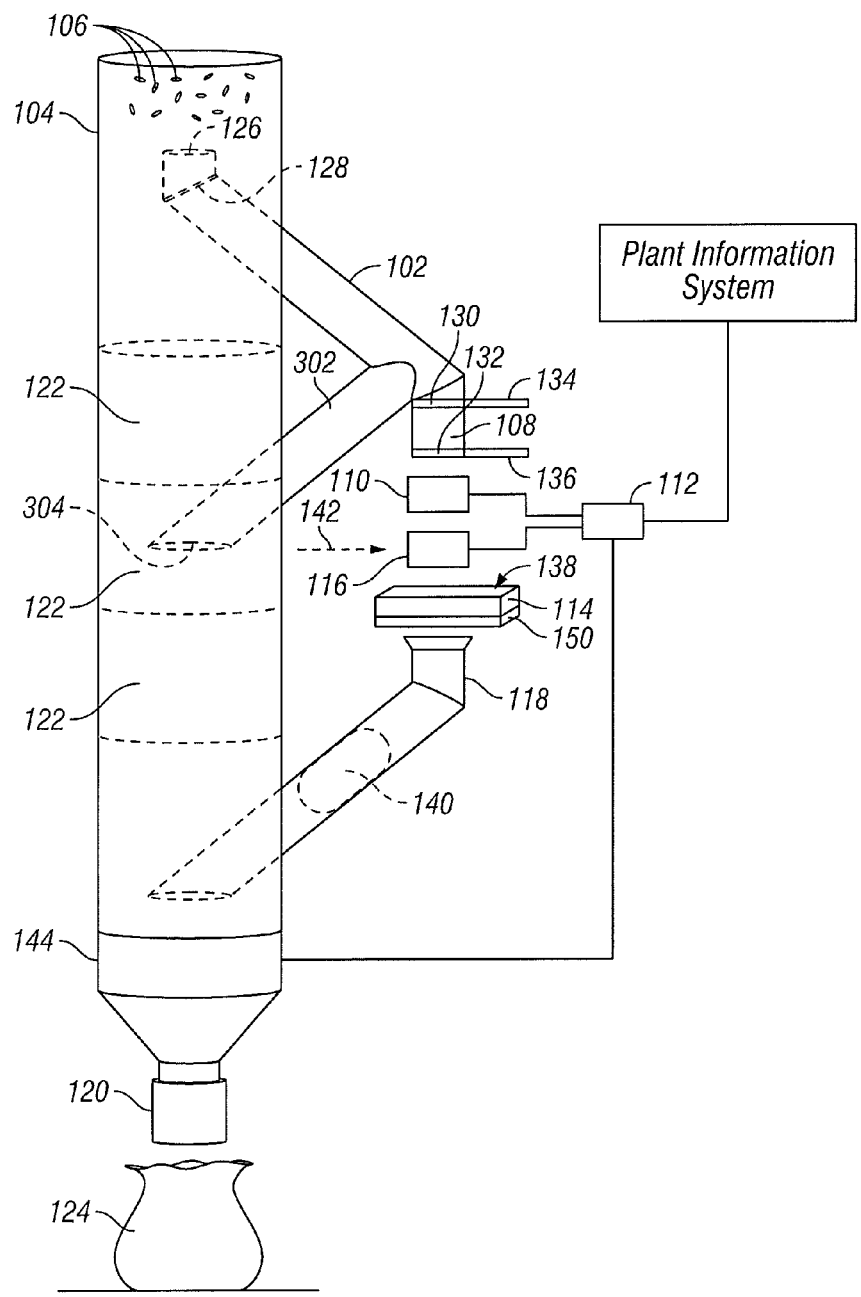
FIG. 3 is an illustration of another embodiment of the present disclosure in connection with an existing product bin, bagger/scale, and bag.

Referring to FIG. 3, a return pipe 302 may be in communication with the sample input piping 102 above the top gate 134 to provide a return to the bin or piping 104 for any products 106 prevented from entering the sampling volume 108, step 208 of FIG. The product 106 contained in return piping 302 may be directed to another part of the bin 104 via connection of return piping 302 to sample output piping 118 or processed otherwise. Alternatively, the return piping 302 may terminate in an opening 304 in the bin 104 which may be positioned to ensure return of the products 106 to the same zone 122 from which it was sampled at the time the zone 122 reaches the opening 204.

Returning to FIG. 1, in the first embodiment, the sampling volume 108 is also in communication with a scale 110, such that when the bottom gate 136 of the sampling volume 108 is opened, after the sampling volume 108 has filled with the products 106 and fixed a sample 140, the products 106 of sample 140 contained therein falls onto the scale 110, step 210, which weighs the sample 140 and provides an output to a processor 112, step 212 of FIG. 2, consistent with, and indicative of, the weight of the sample 140. Scale 110 is therefore adapted to transmit a sample weight value to a processor 112, which may function as a weight processor. The scale 110 may therefore be positioned below the sampling volume 108 and receive the sample 140 from the sampling volume 108.

Figure 4:
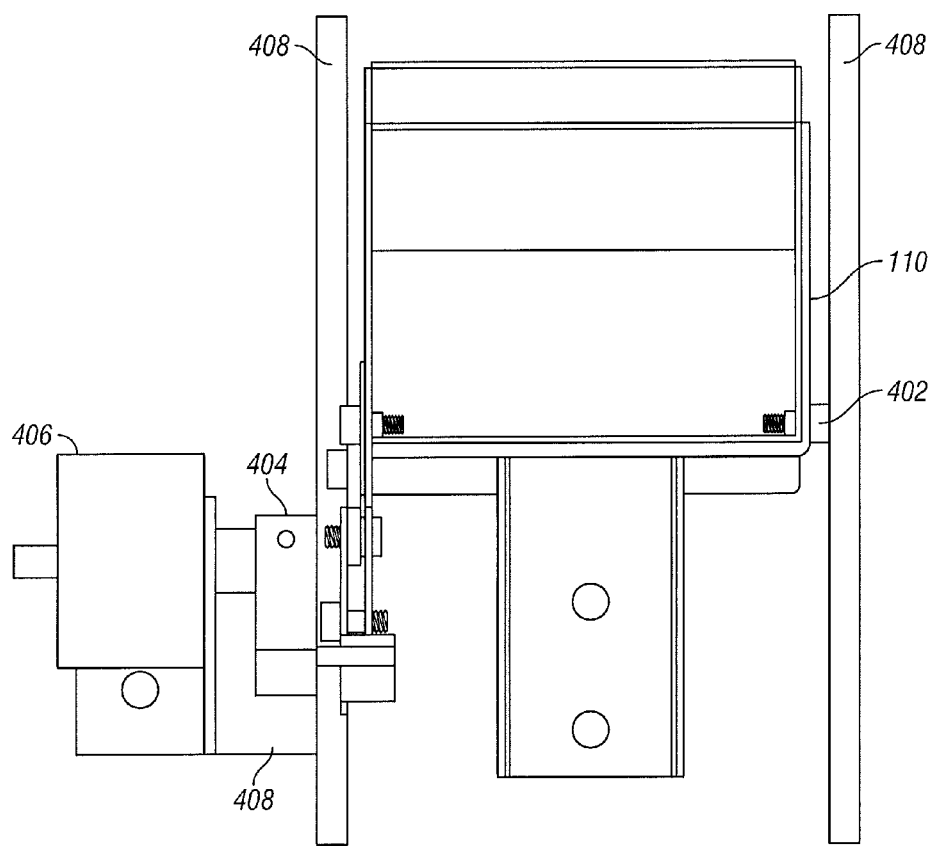
FIG. 4 is an illustration of a scale which used in the present disclosure.

Referring to FIG. 4, the scale 110, preferably constructed to include a bucket, is preferably rotatably mounted to permit the sample 140 contained in the scale 110 to be dispensed onto an imaging table 114 after the processor 112 records the weight associated with sample 140, step 212 of FIG. 2. Scale 110 may therefore be a dump scale. The scale 110 may be hingely mounted by pins 402 connected to a support frame 408 and maintained in position by a rotatable or releasable arm 404 connected to a motor or by piston 406 or may be rotatably mounted and rotated about an axis. Alternatively, the scale 110 may be fixed in position and associated with a closable dispenser, thereby opening and closing the orifice to permit the products 106 associated with the sampling volume 108 in the scale 110 to be dispensed onto an imaging table 114. In a further alternative (not shown), a brush or plow may be associated with scale 110 to push the products off the scale 110 for delivery to the imaging table 114. The imaging table 114 may be positioned below the scale 110 and positioned to receive the sample 140 from the scale 110. In each instance, the scale 110 is preferably emptied in response to a signal from the processor 112, but may be constructed to empty after a uniform time period. For accuracy, the scale 110 preferably is accurate to at least one hundredth of a gram.

Figure 9:
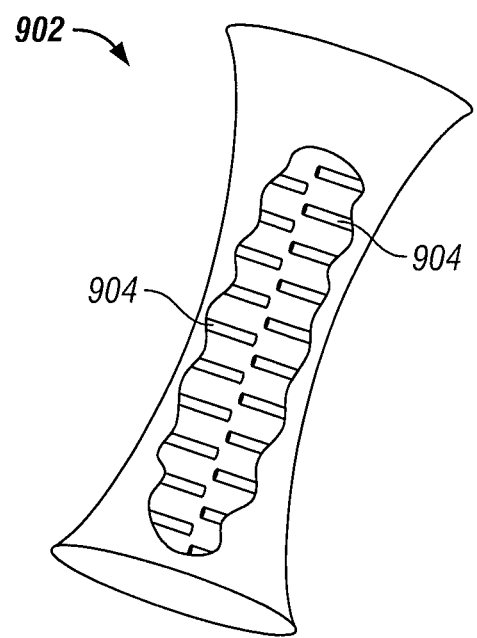
FIG. 9 is an illustration of a damping device which may be placed intermediate the scale and the imaging table.

Due to the position of the products 106 in the sample 140 in the scale 110, products 106 may have increasing potential energy which may be translated to kinetic energy during the dispensing from the scale 110 to the imaging table 114. Thus it may be helpful to include a damping device between the scale 110 and the imaging table 114, such as the damping device 902 depicted in FIG. 9, which dissipates the kinetic energy of the products 106 prior to reaching the imaging table 114. This may be accomplished by, among other options, a damping device 902 which includes a number of protrusions, such as spaced apart bars or pegs 904, as illustrated in FIG. 9. Such protrusions absorb some of the energy of the moving products 106 while only slightly slowing the flow of the products 106 in the sample 140 to the imaging table 114. Alternatively, the damping device 802 may include other materials intended to contact product 106 during its downward descent and thereby slow the product 106, such as rotating paddles or ribbons of material. Alternatively, the damping device may include a textural profile using long screws with plastic heads to retard the velocity of the falling products 106.

Referring again to FIG. 1, once the products 106 of the sample 140 are deposited on the imaging table 114, step 214 of FIG. 2, the sample 140, namely the products 106, are imaged by the camera 116, preferably a monochromatic camera of sufficient resolution to identify the edges of individual products 106, step 216 of FIG. 2. Camera 116 may be dichromatic, black-and-white, or color, or permit vision of two or more color ranges. Preferably, the imaging table 114 is illuminated from below, thus providing high contrast between the surface 138 of the imaging table 114 and the products 106 of sampling volume 108.

In an alternative embodiment, the scale 110 and the imaging table 114 are integrated into a single unit, such that there is no need for step 214 to dispense the sample 140 from the scale 100 to the imaging table 114.

The processor 112 receives one or more images of the imaging table 114 via the camera 116 from which a count of acceptably-sized products 106 contained in sample 140 is determined, step 218 of FIG. 2. Camera 116 must therefore be adapted to transmit at least one image of the content of the image table 114 to a processor 112, which may be a counting processor. The counting processor is adapted to distinguish the products of said sample within a desired color range, to eliminate from identification those products outside the desired color range, and may be adapted to identify at least two counts within the identified number of acceptable products according to two or more colors.

In an embodiment where camera 116 is color camera, at step 218 the processor 112 may further include, within the count of acceptably-size products 106, a count of product within the sample meeting color characteristics, which may result into categorization of products 106 into two or more subgroups, such as off-color and prime, or into resistant and refuge based on treatment coating in refuge-in-bag seed packaging operations. Color count may be desirable where seed color is indicative of desired product 106 versus undesirable product of acceptable size. Use of a color camera permits distinguishing among product, for example, between modified and refuge kernels based on the color of the treatment coating. Further, it becomes possible in such a situation to weigh and count all of the kernels, and to assess the red:green ratio to determine whether it is coated red or green. In other circumstances, a monochromatic camera provides advantages over a color camera as there is no interpolation of pixel values across the Bayer filter inputs. The benefits of monochromatic images are noticeable in soybeans and wheat. In such circumstances, the 8-bit grayscale image is converted to binary (1 or 0) in the threshold step. If the image is color, one of the three planes (R, G or B) is selected and that 8-bit grayscale image is also processed into a binary image by thresholding. The system may further be adapted to use color to assess the defect level (such as off-color product or foreign material) in the product flow, particularly if product is alternatively imaged from top and bottom for comparison purposes, in which embodiment, the product could be illuminated from below, rather than from above, for counting of product, then illuminated from the opposite side so the system could apply an overlay, created from the first image, with color added to each object location and assess the color for each object.

Moreover, at step 218, the method may further include display of the sample count and the display of the image from the camera 116 and adjustment of the sample count, such as by the operator, prior to determination of the product density value. Thus, the operator may override the counting processor if needed.

In an alternative embodiment, the scale 110 and the imaging table 114 are integrated into a single unit, such that there is no need for step 214 to dispense the sample 140 from the scale 100 to the imaging table 114.

Figure 10:
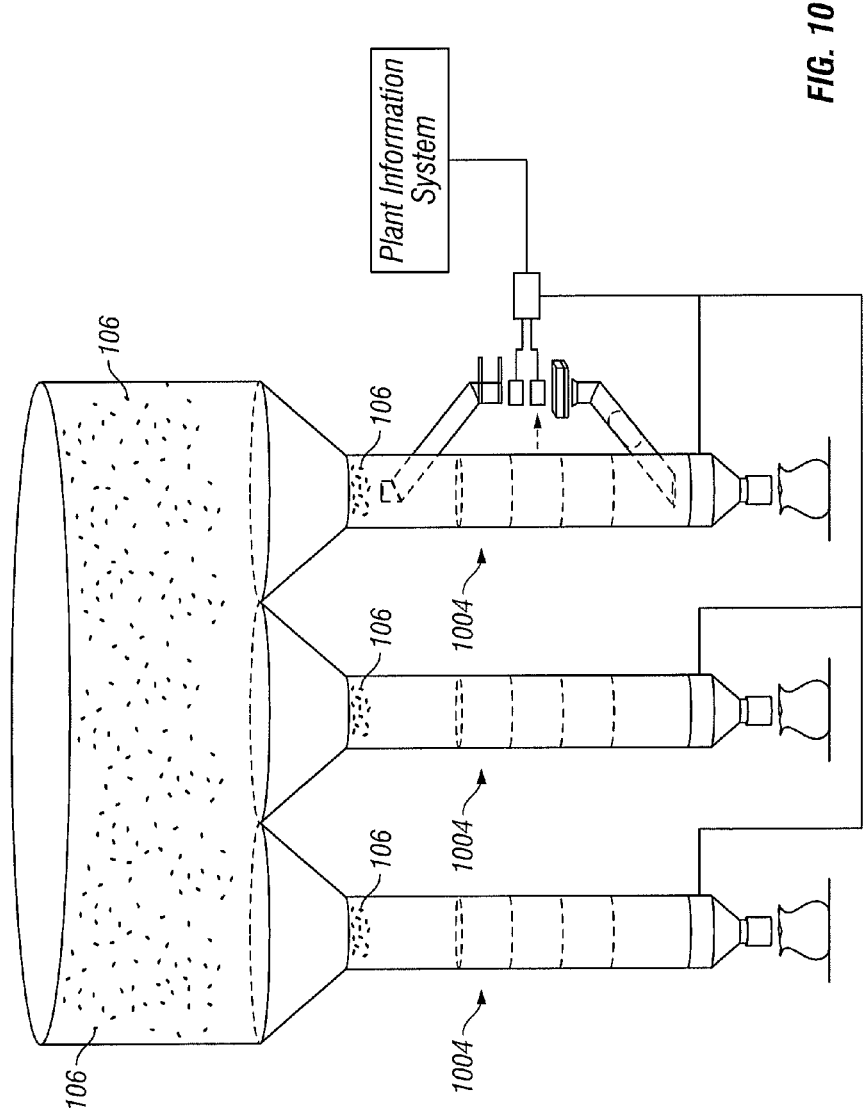
FIG. 10 is an illustration of a parallel flow system with the present disclosure.

In another alternative embodiment depicted in FIG. 10, one or more separate pipings 1002 of products 106 may be operated in parallel with piping 104. Thus, multiple paths of products 106 may be simultaneously used and utilized, all relying on the data from the first path of piping 104.

In operation, the processor 112 determines the number of acceptably-sized products 106 on the imaging table 114 from an image received from the camera 116, based on identification of the edges of the products 106 on the imaging table 114, which identify products 106 within an acceptable size range. The acceptable range of sizes of products 106 may be defined in the processor 112 based on the product being dispensed, or may be determined based on the size of imaged products, i.e., those within a range of sizes within a deviation, preferably those within one standard deviation of the mean size.

Figure 5:
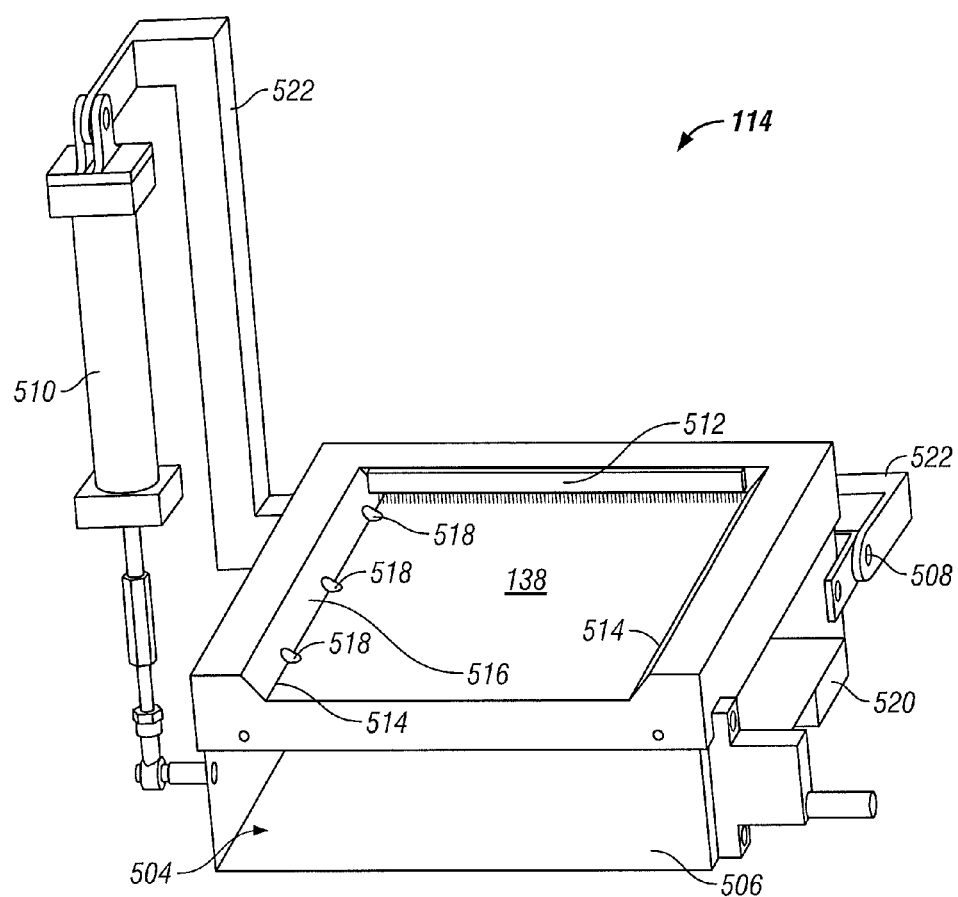
FIG. 5 is an illustration of the imaging table which used in the present disclosure.

The identification of the size of the products 106 is accomplished, in part, due to the construction of the imaging table 114. As depicted in FIG. 5, the imaging table 114 includes a surface 138, which is at least translucent to light and which is illuminated from below. This illumination may be from any light source 504, but preferably one that provides a relatively consistent and sufficiently high level of illumination. Preferably the light source 504, such as a light, such as a plurality of light-emitting diodes, illuminates the imaging surface 138 of the imaging table 114 (an imaging table surface), preferably from above, but if a transparent imaging surface 138 is employed, then alternatively from below. The light from light source 504 is preferably diffused at the imaging surface 138 to provide consistent illumination. This diffusion may be accomplished by a diffuser 506 integrated into the surface 138 or below it. As a result, the diffused illumination at the surface 138 of the imaging table 114, when covered with the products 106, provides an image wherein the products 106 appear in shades of gray against a brighter background, which may be white or gray. Additionally, the light source 504 and the reflected light entering the camera 116 may be cross-polarized to eliminate glare from the imaging table 114 or the products 106. To reduce clumping or layering of the products 106 in the sample 140, the surface 138 of the imaging table 114 may be associated with a vibrating device, such as eccentric motor, thus causing the surface 138 of the imaging surface 138, and the products 106 thereon, to vibrate and thus separate the products 106 from one another to avoid the products 106 clumping together or climbing atop one another.

The imaging surface 138 of the imaging table 114 may include an inclined transparent lip or ridge 516 about the surface perimeter 514 of the imaging table 114, on which the products 106 cannot rest, to better provide an extensive translucent surface for the imaging surface 138 and avoid the potential for the edge of a product 106 to be adjacent a non-translucent surface such as the edge of the imaging table 114, which would create difficulty in identifying the edges of the products 106. Moreover, the inclined transparent lip or ridge 516 may be raised sufficiently, or may have extended sides, to prevent the products 106 from bouncing off the imaging table 114 when transferred from the scale 110. Additionally, the imaging table 114 may include one or more air jets 518 aimed the imaging surface 138 at or near the corners of lip or ridge 516 to better force products 106 away from the edges of imaging table 114. The vibratory motor 520 or other device may also be used to shift the products 106 about the imaging table 114 between images from camera 116, thus providing a different presentation of products 106 for subsequent review. The vibratory motor 520 or other device may be connected to the imaging table 114.

Referring to FIG. 1, the acceptable-size of the products 106 used for identification may be pre-programmed, or may be determined by the processor 112 as the mean size of the products 106 initially identified by the processor 112 upon review of data from camera 116.

Additionally or alternatively, the imaging surface 138 of the imaging table 114 may be illuminated by a light 142 for assessment of the products 106 deposited on the imaging table 114. Preferably light 142 provides broad spectrum lighting, which may generally be white light, and may be characterized as warm white light. Alternatively, light 142 may provide light in as few as two wavelengths. Light providing a plurality of wavelengths is beneficial as various products 106 may reflect at different wavelengths when exposed to broad spectrum lighting. Foodstuffs, for example, contain more red than blue. It is important light 142 provide each of the red, green and blue wavelengths so that all pixels filled by a camera 116 respond to the sample 140 being viewed.

When used, the data from the camera 116 is assessed, by processor 112 to identify those areas of the imaging table 114 which are covered by an object sufficiently different in color, which may be bad products (such as rotted seed), rocks, or other contaminates. They may be seeds of different genetic properties indicated by different colors of coating. These objects can be subtracted or eliminated from the image by processor 112 before identification or assessment of the mean product size and/or the counting of products.

Returning to the product count, in determining the product count, clusters of products, which generate an image clearly beyond the accepted distribution from the acceptable product size, are not counted. Similarly, broken products or other undesirable constituents, to the extent not already removed, will not be counted to the extent they are below the accepted distribution from the acceptable seed size. This is accomplished by processing of the image by processor 112, which is adapted to identify each acceptable product 106 in the sample 140 within the acceptable product size range and to determine the number of acceptable products 106. In one embodiment, the raw image of the sample 140 from camera 116 may be converted to a binary image having a threshold value, such as 30. The binary image may then be processed to find all connected regions, and to identify all isolated products 106 and clusters of four or more products 106.

Figure 6:
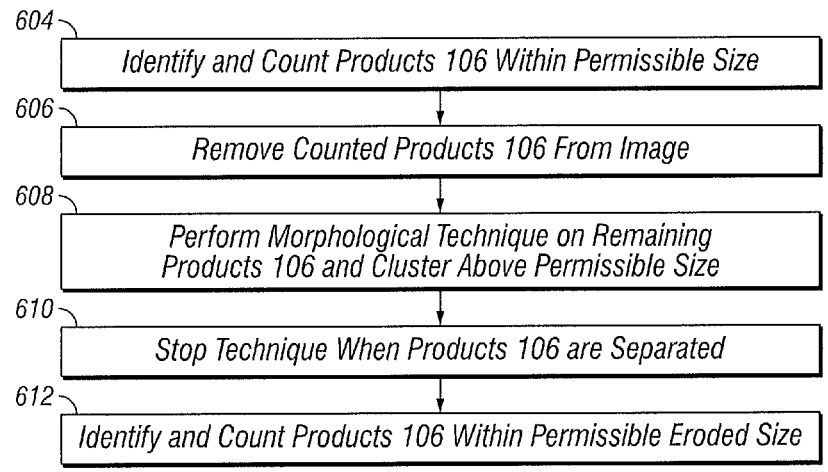
FIG. 6 is a flowchart of the steps used associated with the processing of an image from the imaging table.

Referring to FIGS. 1 and 6, once those products 106 fitting within the acceptable product size range are counted, step 604 of FIG. 6, processor 112 filters the image, first removing the image of those products 106 which were counted and those that fall below the acceptable product size, step 606, i.e., subtracting those areas, and then using a known morphological technique, such a erosion, to reduce the size of the products 106 in the remaining product clusters in the image, step 608, until the image of the products 106 is sufficiently eroded for a further count, step 610, i.e. to perform a morphological erosion on the image of those products 106 above the acceptable size range until all of the products 106 above said acceptable size range appear separated or in predictable count clusters. The processor 112 is thus able to determine the number of separated products 106 and the number of products 106 in predictable count clusters. In a further embodiment, the processor 112 may be adapted to mark the eroded products as discrete individuals, then to dilate the image using the same structuring factor to return the identified product 106 to their original size, but recognized as discrete products 106. Thus, in the further embodiment, the remove-singles-and-erode process may be performed but seeing the previously marked products 106 as full size. In an alternative embodiment, a dilation step may be added after the products 106 are separated, providing the advantage of restoring the products 106 to original size in the original image. While not essentially, without this step, the exact size and shape used in the analysis will vary based on how much the erosion step 608 has reduced the object. Depending on the surroundings, two clusters of the same size may erode differently and have differing, potentially only slightly, geometric characteristics. Processor 112 must therefore be adapted to at least perform morphological erosion on the image of the products 106 outside the acceptable size range until at least some of the products 106 above the acceptable size range appear separated and be adapted to determine the number of separated eroded images of products 106. Clumps or collections of products 106 are therefore reduced to individual product images. In one embodiment, this may be accomplished by eroding the image by a structuring factor of 4.0, to provide nearly complete isolation of individual objects, leaving potentially only a few non-singulated products 106, small enough to be characterized in the count algorithm. The processor 112 then counts the identified products 106, step 612, repeating the process of erosion, step 608, assessment, step 610, and counting products 106 on the image, step 612, on the image until all products 106 have been removed. Ideally no more than six repetitions are performed on an image due to time constraints. Processor 112 may then combine the number of acceptable products 106 within the sample 140 within the acceptable size range, the number of separate products identified by the erosion, and the number of products in predictable count clusters, to determine a sample count.

To reduce error, the process, steps 606-612, may be repeated on a further copy of the image or multiple images recorded or photographs taken, potentially with different structuring elements to provide potentially differing product counts. A statistical point in the distribution of the identified product count(s) may then be used, which may be the mean, a point below the mean, thus providing a higher approximate product count, or a point above the mean, thus providing a lower product count.

Where the morphological operation used is erosion, pixels are removed on object boundaries. As is known, the number of pixels added or removed from the objects in an image depends on the size and shape of the structuring element used to process the image. For most products, a circular matrix is sufficient; however in some instances a perpendicular intersection of two lines is better. The latter, for example, is helpful in erosion of an image of corn kernels, largely due to the variation in kernel size and irregular geometry. In cases of uniform geometry such as with soybeans, some portion of the objects in the view may be isolated and fall within the acceptable size range. These objects are counted as singles and can be removed from consideration before the erosion process begins. The remaining objects will be eroded and reevaluated. At this point, size alone is not sufficient to determine the count because a cluster of two seeds may have been eroded to an area within the acceptable size range. Other geometric properties must be used to determine the object count. It is well known that the relationship between area and perimeter can be useful in evaluating geometry. Roundness is also a powerful discriminator. Threshold values can be established for reliable discrimination between clusters of two, three or four seeds. Larger clusters may not be reliably counted, so an additional erosion step may be applied and the algorithm applied to the resulting images. This process may be repeated until the largest cluster is small enough to be reliably measured. In the specific case of medium size soybeans imaged at a scale of 75 pixels per inch, the algorithm [[perimeter/roundness squared]×[area/1000]] yields a parameter that reliably predicts the number of seeds in a cluster. Parameter values below 6 indicate a single seed, between 6 and 75 two seeds, between 75 and 150 three seeds between 150 and 500 four seeds. Values above 500 indicate a larger cluster and the need for more erosion.

For objects which are not uniformly round the parameter roundness may not be a useful discriminator. Other geometric properties such as axis ratio, the relationship between the largest inner circle and the smallest outer circle have been shown to improve discrimination. While there are some common elements in the algorithm selection for a specific seed based on its shape, each seed such as soybean, corn, cotton, pumpkin, rice, etc. each must be evaluated independently to determine the most effective algorithm.

Figure 7:
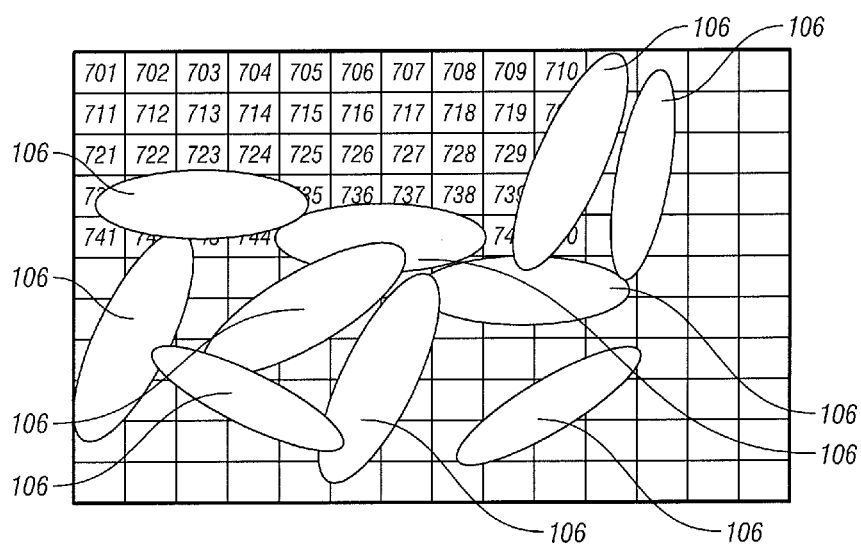
FIG. 7 is a graphical depiction of an image from the imaging table as part of morphological processing.
Figure 8:
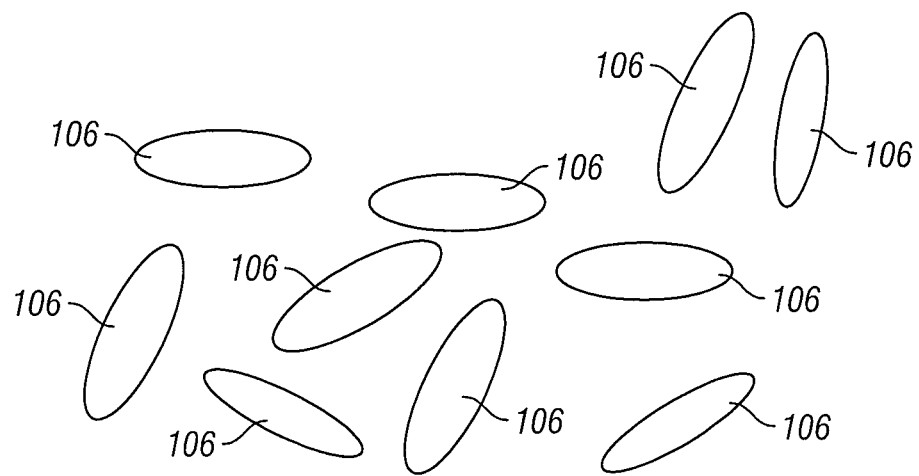
FIG. 8 is a graphical depiction of an image from the imaging table after morphological processing.

In cases where the geometry is very irregular another approach may be needed. The processor 112 may assess each pixel or grid section in the image based on the surrounding pixels. The grid size applied by the processor is defined by the user and is typically a grid created by two perpendicular axes. As depicted in FIG. 7, because of the contact between the various products 106, and therefore the edges touching and forming one continuous object, on the imaging surface 138, processor 112 may initially determine only two products are present. As depicted in FIG. 7, when processor 112 assesses cell 742 based on a circular matrix, it considers whether all cells 731, 732, 733, 741, 743, 751, 752 and 753 contain data, part of a product 106, a binary "1". As cell 741 does not contain data but rather is empty, the value of cell 742 is determined to be set to zero upon completion of the assessment; i.e., all data removed, of the entire image, thus eroding the edge of product 106 associated with cell 742 in the revised image. The processor 112 then continues across the image to the next cell, 743, and assesses the cell based on the original image. The processor 112 then assesses the eroded image to determine the number of products 106 present, which have been reduced in size and, hopefully, separated from the former clusters by erosion of the associated edges of the products 106 in the cluster. The result is identification of the products present, such as on FIG. 8, which after erosion through one or more iterations, separates the products 106 to identify the actual count of ten (10) products 106. For those clusters not separated by the first erosion, further erosions may be performed on the image(s) until all clusters of products have been reduced to individual product images. The speed and accuracy of this erosion can be adjusted based on the resolution of the camera 116 used and the size and configuration of the matrix used for erosion.

Additionally, where one or more clusters, such as three product cluster, of product 106 is identified, the eroded image may be altered, potentially reblobbed, such that the previously connected objects are now identified as separate objects and then dilated back to the previous image. The products 106 touching one another can still be recognized as individuals and counted.

The few non-singulated products 106, generally clusters of two or more products 106, can be evaluated based on the count algorithm, where the discriminator is a function of perimeter, roundness and area, such as perimeter/roundness/roundness*area/1000. For example, given a two-seed objection having a perimeter of 63.11, roundness of 0.700 and area 232, the calculation of perimeter (63.11) divided by roundness (0.700) divided by roundness (0.700) times area (232) has a value of 29.86, which if used in connection with a 2:3 threshold of 75, will be counted as two seeds. Similarly, given a four-seed object having a perimeter of 117.4, roundness of 0.606 and an area of 502, the calculation of perimeter (117.40) divided, by roundness (0.606) divided by roundness (0.606) times area (502) has a value of 160.41, above a 3:4 value of 150 and thus counted as four seeds.

The system may provide a visual confirmation to the operator, where the original image is presented with an overlay showing the counted clusters, which may be color coded to identify the number of products 106 determined to be present in a cluster. The operator may, after reviewing the data, determine a threshold differentiating between adjacent cluster sizes is inaccurate and should be adjusted. This is particularly true when the system is first being calibrated for a particular product 106.

Referring to FIG. 5, imaging table 114 is preferably rotatably mounted to permit the products 106 associated with the sampling volume 108 imaging table 114 to be dispensed to a sample output piping 118, with which imaging table 114 is in communication, after processor 112 determines the count of products 106 of sampling volume 108, step 220 of FIG. 2. Imaging table 114 may be hingely mounted on pivots 508 connected to a support frame 522 and maintained in position by a piston 510 attached to the imaging table 114 and the support frame 522 or may be rotatably mounted and rotated about an axis. In a further alternative, a brush 512 or plow may be associated with imaging table 114 to push the products 106 off the imaging table 114 for delivery to the sample output piping 118 or to ensure all products 106 are removed from the imaging table 114. In each instance, the imaging table 114 is preferably emptied in response to a signal from the processor 112, but may be constructed to empty after a uniform time period. Alternatively, a pneumatic system may push or pull (suck or blow) products 106 from imaging table 114.

Referring to FIG. 1, after products 106 of sampling volume 108 are removed from the imaging table 114 and communicated to sample output piping 118, which may return the products 106 to the bin or piping 104.

In an alternative embodiment, the system may be a unit constructed for use in a laboratory application, thus providing the same data benefit, but driven by an operator.

Returning to FIGS. 1, 2, and 3, once a count of products 106 in the weight of sample 140 is known, the product density value of the products 106 associated with a zone, such as zone 122 is established by dividing the sample count, step 220 of FIG. 2, by the sample weight, step 212 of FIG. 2, which is accomplished at step 222 of FIG. 2. Density may be determined in a processor 112, which may be a density processor adapted to determine the product density value of a zone of preferable small fungible products within an acceptable size range by dividing the sample count by the sample weight value. Beneficially, as the time for obtaining the sample weight, step 212 of FIG. 2 and the sample count, step 220 of FIG. 2 can be quite short, the product density value may be obtained rapidly, such as nearly instantaneously, which may also be referred to as obtaining the product density value in real time, or in near real-time. The density processor may be adapted to receive an input of the sample weight directly from the scale 110 or may be received from other input devices, such as a keyboard or touch-sensitive device, such as a touch screen.

As a result, where the system is integrated into a flowing product supply, the product density value of a zone 122 in bin 104 may be determined in less than a minute, and preferably the value of product densities of three nearby zones 122 may be obtained within a minute. Desirably, the time frame should be less than five seconds. Most particularly, the product density value of a zone 122 in a flow of products 106 is ideally determined and output to a product flow controller 144 controlling a flow control device, such as the bagger/scale 120 or a gate, before the zone 122 reaches the flow control device, thus providing the product density value in real time. When needed, a desired minimum weight associated with the desired quantity may be obtained by dividing the desired quantity by the product density value, step 224 of FIG. 2. In those instances when an automated bagger is associated with and directly connected to the system, which is not required, when the products 106 of the zone 122 associated with the sampling volume 108 reach the bagger/scale 120, the processor 112, which may be a bag-weight processor, activates the bagger/scale 120 and receives a signal from bagger/scale 120 associated with the weight reading output from the bin or piping 104, step 226 of FIG. 2. The processor 112, as a bag-weight processor, is adapted to determine the desired weight associated with a desired quantity of product by dividing said desired quantity by said product density value. When the weight reading output from the bagger/scale 120 to the processor 112 reaches the weight associated with the desired product count, bagger/scale 120 ceases to feed product 106 to the bag 124, step 228 of FIG. 2. Thus, the bagger/scale 120 is adapted to transmit the actual bag weight to the processor 112, which is adapted to compare the actual bag weight to said desired weight. The processor 112 is further adapted to terminate operation of the bagger/scale 120 when the actual bag weight is equivalent to the desired weight.

A larger product plant-based system may alternatively receive the product density value data and, via a product flow controller 144, control the bagger/scale 120. Thus the density calculation may be accessed by a plant information system or an automated packaging system. Similarly, the desired weight may be displayed on a display associated with a manual bagger, permitting the operator to feed the correct weight of product into the bag. Further, the data associated with a zone 122, and therefore with a product from a particular supplier or a particular hybrid, may be retained in a product plant-based system for historical purposes or quality control, such as average size, quality of product, or percentage of contaminants, thus providing storage of at least one image of a sample. Thus, the imaged information may be stored for future analysis, audit support, and process improvement activities in a storage component, such as computer-readable media, such as hard drives, diskettes, and flash memory. Additionally, the system may provide storage of said product density value for access by a plant information system or an automated packaging system. With such data, the plant operator can better select suppliers and ensure higher quality product and lower contamination, which slows processing and increases cost.

As can be appreciated, this weight and imaging process permits the product density value to be determined several times per minute, resulting in data in real-time or near real-time, i.e., at approximately the same time the product 106 passes through the system without substantial delay, thus permitting the operation of any equipment on the product flow line, such as a bagger/scale 120, to be operated at the time the zone 122 associated with the sample 140 reaches the equipment, thus avoiding or addressing potential variations of product density value in various zones 122 in bin or piping 104.

Alternatively, the system may be embodied in laboratory or test environment such that the plant-specific components are not included, such as the bagger/scale 120. Instead, the system may be reduced in size, retaining the required components, and thus providing assessment on the fly of desired samples.

A further embodiment of the disclosure may permit identification of additional characteristics associated with the products 106 in a sample 140 generated from a sampling volume 108. This may include identification of one or more of count-per-weight, of volume-per-weight and/or surface area-per-weight. One or more of these characteristics may be determined. Additionally, this may include identification, for each identified individual product 106, its major and minor axis for later data review. While the third axis (height) cannot be determined from the image captured by the camera 116 of the product 106 on the imaging table 114, the third axis may be assumed, depending on product type, on a percentage of the second axis. In the case of spherical product, such as peas, this may be 100%, while for other products, such as soybeans, the fraction may be lower, utilizing correlations generally known in the art or which may be readily determined.

Figure 11A:
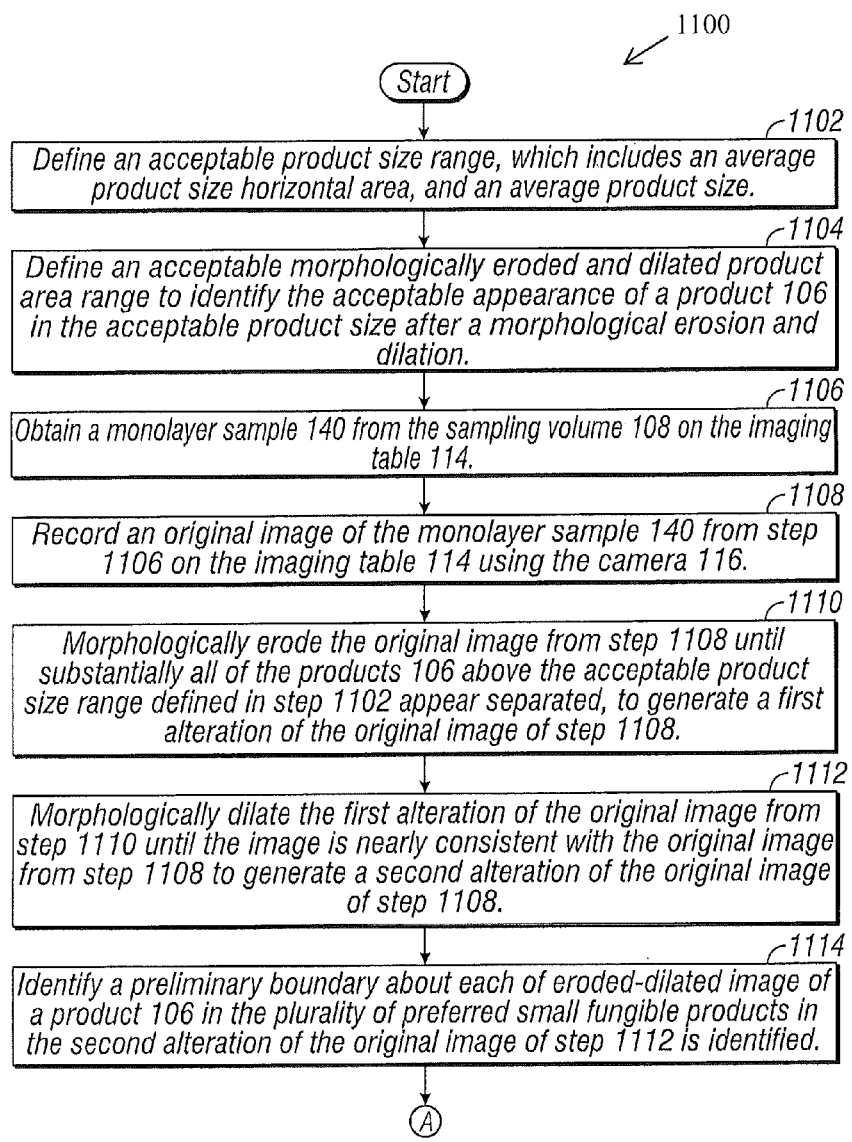
FIG. 11A is a flowchart of the steps used with the present method.

Referring now to FIG. 11A, a flow diagram of a further embodiment of a method 1100 for implementing the present disclosure, and therefore for determining characteristics for a plurality of preferred small fungible products, or objects, in a volume of objects, is illustrated.

In step 1102, an acceptable product size range, which includes an average product size horizontal area, and an average product size are defined by using a client interface or by access to a stored table.

In step 1104, an acceptable morphologically eroded and dilated product area range is defined to identify the acceptable appearance of a product 106 in the acceptable product size after a morphological erosion, reducing the appearance of the product 106, and subsequent dilation, enlarging the appearance of the eroded product 106. This may be defined by using a client interface or by access to a stored table.

In step 1106, a monolayer sample 140 is obtained from the sampling volume 108 on the imaging table 114 as provided above.

In step 1108, an original image of the monolayer sample 140 from step 1106 on the imaging table 114 is recorded or captured using the camera 116 as provided above.

In step 1110, the original image from step 1108 is morphologically eroded, such as provided above, until substantially all of the products 106 above the acceptable product size range defined in step 1102 appear separated, to generate a first alternation of the original image of step 1108. Ideally all products 106 should appear singular after erosion; however, this may not occur where products 106 are closely clustered, resulting in areas which may be recognized as clusters and in singulated products. Erosion continues until most, but not necessarily all, product 106 appear singulated. Properties of clusters may be determined or may be extrapolated based on properties of singulated products 106.

In step 1112, the first alteration of the original image from step 1110 is morphologically dilated, such as provided above, until the image is nearly consistent with the original image from step 1108 to generate a second alteration of the original image of step 1108. The second alteration of the original image thus contains an eroded-dilated image of each of the plurality of the preferred small fungible products 106. This second alteration of the original image is composed of a plurality of pixels, wherein each of those pixels has an intensity with a first intensity range. Each of these pixels may have a color depth, which may be greater than sixteen (16) bits, but need not be so.

In step 1114, a preliminary boundary about each of eroded-dilated image of a product 106 in the plurality of preferred small fungible products in the second alteration of the original image of step 1112 is identified.

Figure 11B:
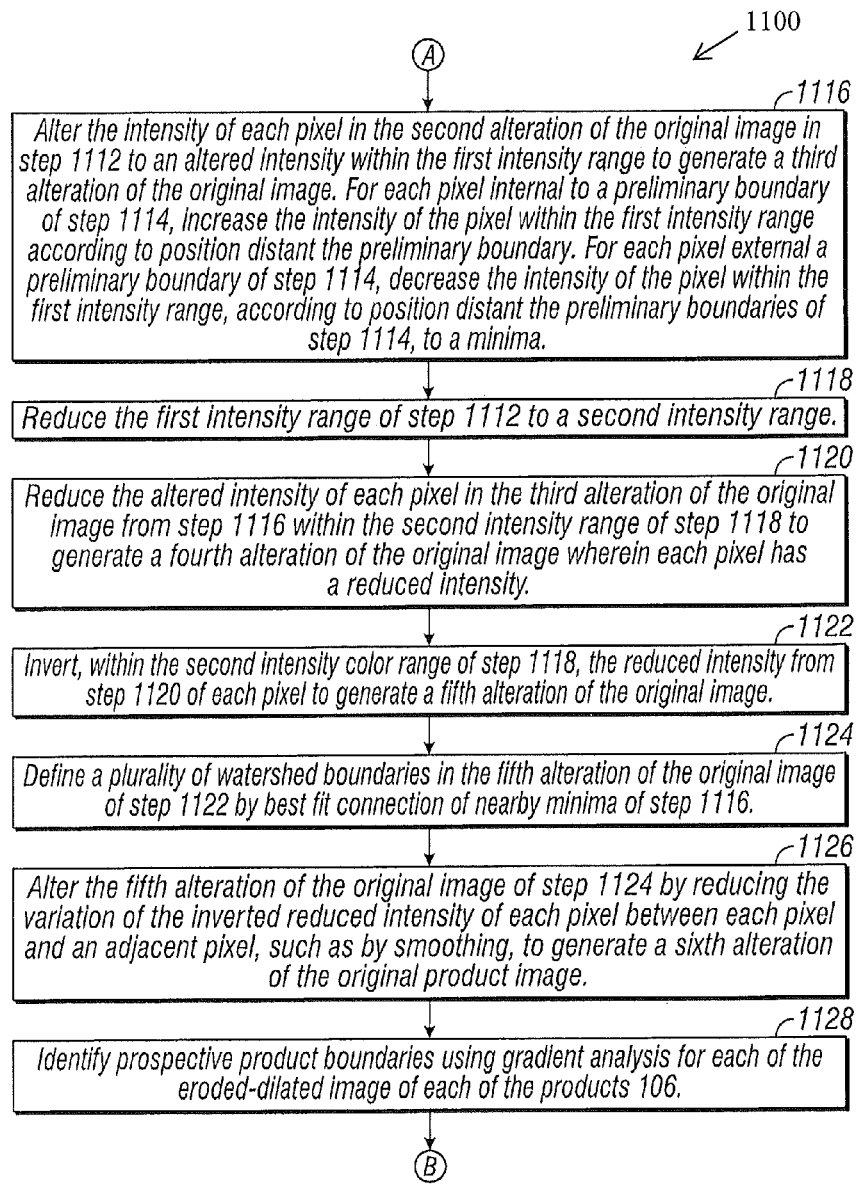
FIG. 11B is a continuation of the method illustrated in FIG. 11A.

The method 1100 continues to FIG. 11B. In step 1116, the intensity of each pixel in the second alteration of the original image in step 1112 is altered to an altered intensity within the first intensity range to generate a third alteration of the original image. For each pixel internal to a preliminary boundary of step 1114, the intensity of the pixel is increased, within the first intensity range, according to position distant the preliminary boundary. For each pixel external a preliminary boundary of step 1114, the intensity of the pixel is decreased, within the first intensity range, according to position distant the preliminary boundaries of step 1114, to a minima. Thus, the intensity of a pixel increases the closer the pixel is to the center of the preliminary boundary and decreases, outside a preliminary boundary, the greater the distance is to nearby preliminary boundaries.

In step 1118, the first intensity range of step 1112 is reduced to a second intensity range.

In step 1120, the altered intensity of each pixel in the third alteration of the original image from step 1116 is reduced within the second intensity range of step 1118 to generate a fourth alternation of the original image wherein each pixel has a reduced intensity. In step 1120, the color depth of each pixel in the third alteration of the original image from step 1116 may be reduced, such as to sixteen (16) bits, if the color depth in the third alteration of the original image from step 1116 is greater than the desired color depth.

In step 1122, the reduced intensity from step 1120 of each pixel, within the second intensity range of step 1118, is inverted within the second intensity color range of step 1118 to generate a fifth alteration of the original image.

In step 1124, a plurality of watershed boundaries is defined in the fifth alteration of the original image of step 1122 by best fit connection of nearby minima of step 1116. As the fifth alteration of the original image of step 1122, due to the alteration of pixel intensity, resembles a topographical map, the minima of step 1116 may be viewed as providing troughs or valleys between preliminary boundaries of step 1114. Connecting these minima of step 1116 defines likely separations among the products 106.

In step 1126, the fifth alteration of the original image of step 1124 is altered by reducing the variation of the inverted reduced intensity of each pixel between each pixel and an adjacent pixel, such as by smoothing, to generate a sixth alteration of the original product image. Steps 1110-1126 may be consolidated or replaced with other systems to morphologically erode, dilate, and adjust the original image to obtain a plurality of preliminary boundaries in an altered image.

In step 1128, prospective product boundaries are identified using gradient analysis for each of the eroded-dilated image of each of the products 106.

Figure 11C:
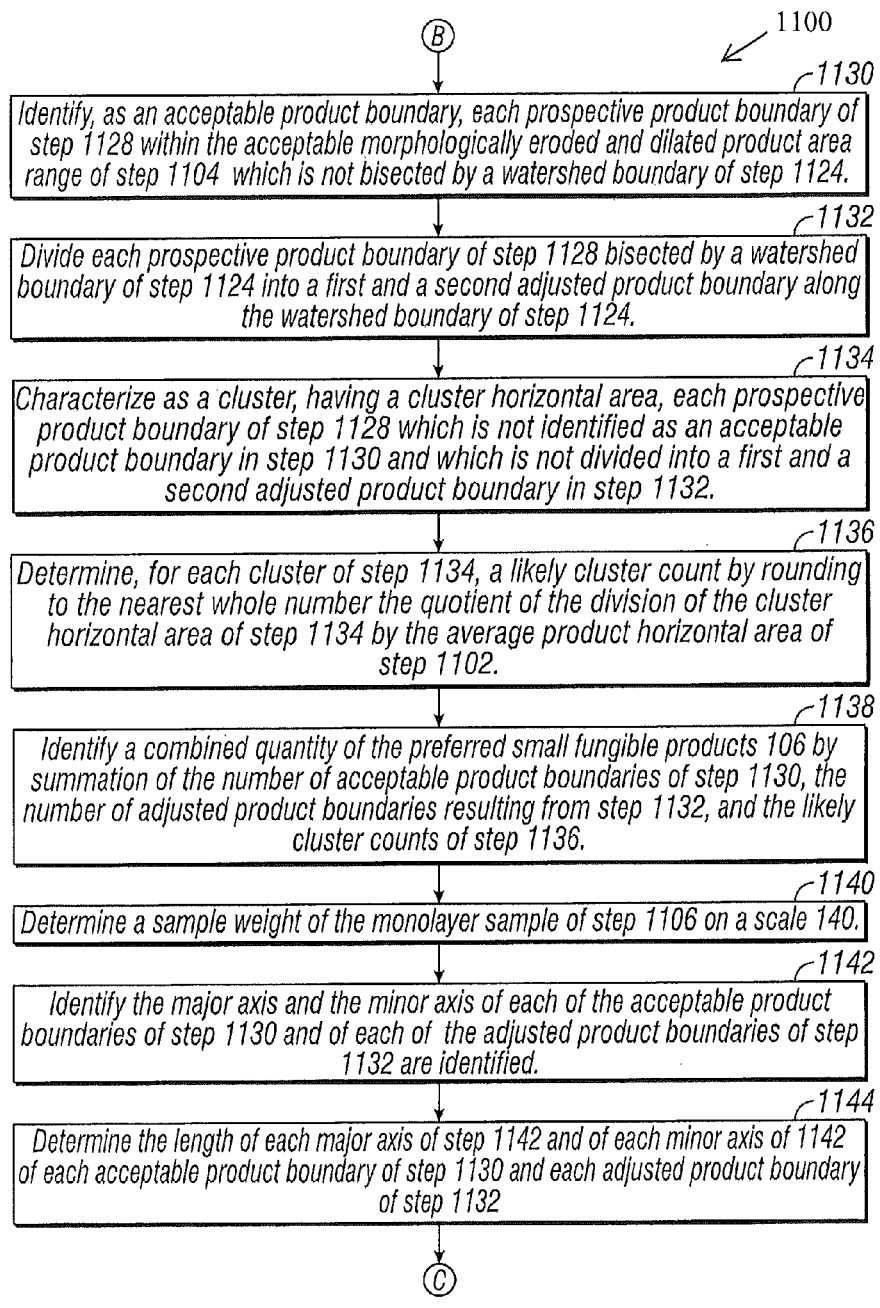
FIG. 11C is a continuation of the method illustrated in FIG. 11B.

The method 1100 continues to FIG. 11C. In step 1130, each prospective product boundary of step 1128 within the acceptable morphologically eroded and dilated product area range of step 1104 which is not bisected by a watershed boundary of step 1124 is identified as an acceptable product boundary.

In step 1132, each prospective product boundary of step 1128 bisected by a watershed boundary of step 1124 is divided into a first and a second adjusted product boundary along the watershed boundary of step 1124. Thus, where two adjacent products 106 are so close as to preclude singulation by erosion and dilation, the method 1100 divides the two adjacent products 106 along the watershed boundary of step 1124, and adopts that division along the watershed boundary of step 1124 as a portion of the boundary of the first and the second adjusted product boundary.

In step 1134, each prospective product boundary of step 1128 which is not identified as an acceptable product boundary in step 1130 and which is not divided into a first and a second adjusted product boundary in step 1132 is characterized as a cluster, wherein each cluster has a cluster horizontal area.

In step 1136, for each cluster of step 1134, a likely cluster count is determined by rounding to the nearest whole number the quotient of the division of the cluster horizontal area of step 1134 by the average product horizontal area of step 1102.

In step 1138, a combined quantity of the preferred small fungible products 106 is identified by summation of the number of acceptable product boundaries of step 1130, the number of adjusted product boundaries resulting from step 1132, and the likely cluster counts of step 1136. The method 1100 may stop here, or may proceed further.

In step 1140, a sample weight of the monolayer sample of step 1106 is determined on a scale 140.

In step 1142, the major axis and the minor axis of each of the acceptable product boundaries of step 1130 and of each of the adjusted product boundaries of step 1132 are identified.

In step 1144, the length of each major axis of step 1142 and of each minor axis of 1142 is determined.

Figure 11D:
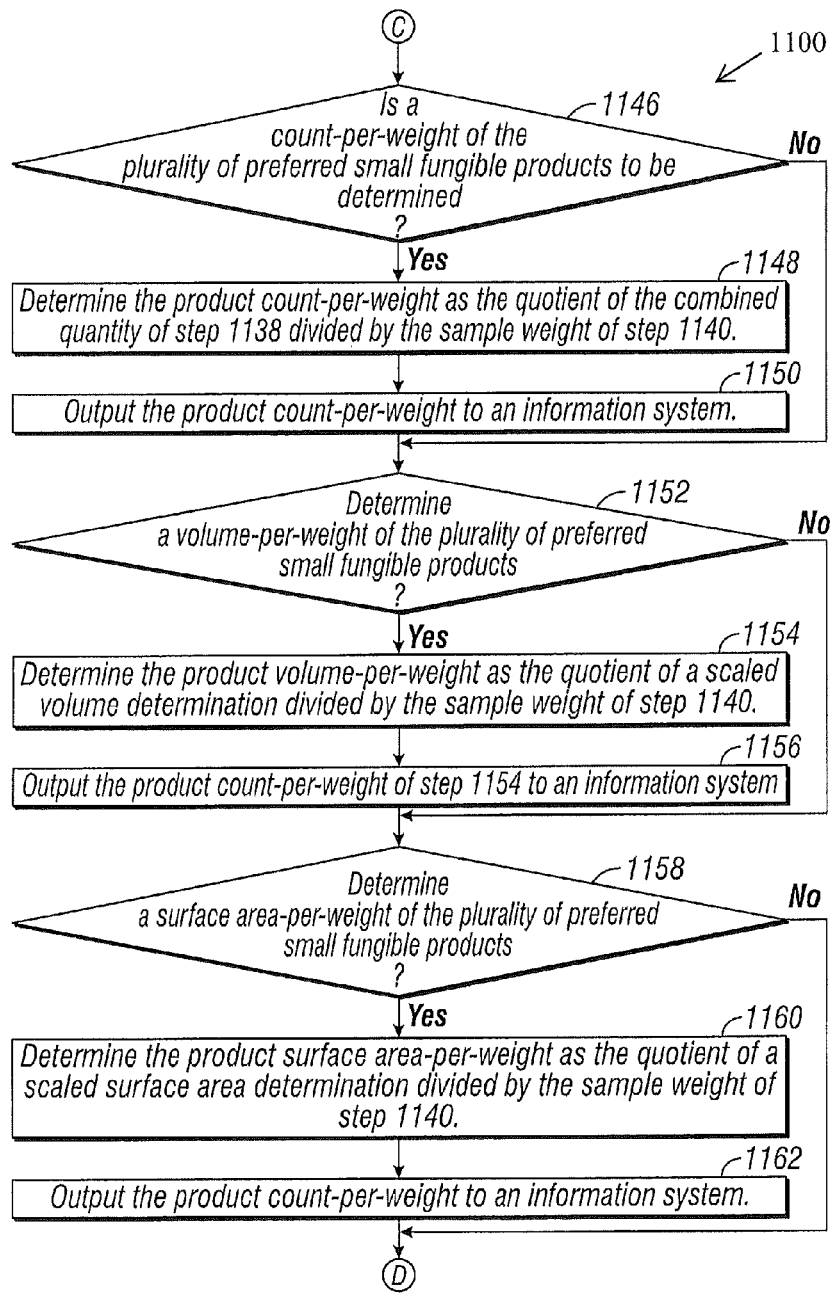
FIG. 11D is a continuation of the method illustrated in FIG. 11C.

The method 1100 continues to FIG. 11D. In step 1146, the method 1100 determines whether to determine a count-per-weight of the plurality of preferred small fungible products. If no count-per-weight is to be determined, then the method 1100 proceeds to step 1152. If the count-per-weight is to be determined, then the method 1100 proceeds to step 1148.

In step 1148, the product count-per-weight is determined as the quotient of the combined quantity of step 1138 divided by the sample weight of step 1140. This product count-per-weight may be used, as provided above, in connection with a bagging system.

In step 1150, the product count-per-weight is output to an information system, which may permit later further review of the product count-per-weight of step 1148.

In step 1152, the method 1100 determines whether to determine a volume-per-weight of the plurality of preferred small fungible products. If no volume-per-weight is to be determined, then the method 1100 proceeds to step 1158. If the volume-per-weight is to be determined, then the method 1100 proceeds to step 1154.

In step 1154, the product volume-per-weight is determined as the quotient of a scaled volume determination divided by the sample weight of step 1140. The scaled volume determination is necessary to address both the lack of an actual third dimension value required for volume computation and the presence of the likely cluster count of step 1136. As a result, the scaled volume determination is the product of a volume determination and a scaling factor. The scaling factor compensates for the lack of detail by assuming the product 106 in the likely product cluster counts of step 1136 are consistent with the average of the products 106 associated with the acceptable product boundaries of step 1130 and with the number of adjusted product boundaries resulting from step 1132. The scaling factor is therefore the quotient of the combined quantity of step 1138 divided by the summation of the acceptable product boundaries of step 1130 and with the number of adjusted product boundaries resulting from step 1132. This scaling factor will therefore be equal to, or greater than 1. The volume determination is a function of the major axis length of step 1144 and the minor axis length of step 1144. While product-specific volume equations have been determined for many types of products 106, for many products, the volume determination can be obtained by assuming an ellipsoidal volume. The volume of an ellipsoidal body is well known:

$$V=(4/3)\pi(\tfrac{1}{2}\text{ major axis length})(\tfrac{1}{2}\text{ minor axis length})(\tfrac{1}{2}\text{ third axis length})$$

This equation provides proper values even if the product 106 is a sphere or an oblate or prolate spheroid. As the method 1100 does not obtain an actual thickness value, although an average value could be obtained by utilizing a second camera 116 positioned in the y-axis, a scaled third axis length may be obtained by the product of the minor axis length of step 1144 and a product-specific scaling factor between 0.0 and 1.0. This scaling factor is known to be no greater than 1.0 as each product 106 settles to a stable position on the imaging table 114, which typically results in the smallest axis length being the thickness of the product. Because the general geometry of a product 106 is consistent within a type of product, regardless of the size of the product 106 within a group, the relationship between the length of a product's minor axis of step 1144 and the length of its third axis can be readily determined from materials known in the art or can be determined based on observation of a sample of product 106. As a result, the volume determination is the sum of the ellipsoidal volumes of each acceptable product boundary of step 1130 and each adjusted product boundary resulting from step 1132 using, for each, the length of its major axis, the length of its minor axis and the length of the scaled third axis.

In step 1156, the product count-per-weight is output to an information system, which may permit later further review of the product volume-per-weight of step 1154.

In step 1158, the method 1100 determines whether to determine a surface area-per-weight of the plurality of preferred small fungible products. If no surface area-per-weight is to be determined, then the method 1100 proceeds to step 1164. If the surface area-per-weight is to be determined, then the method 1100 proceeds to step 1168.

In step 1160, the product surface area-per-weight is determined as the quotient of a scaled surface area determination divided by the sample weight of step 1140. The scaled surface area determination is necessary to address both the lack of an actual third dimension value required for surface area computation and the presence of the likely cluster count of step 1136. As a result, the scaled surface area determination is the product of a surface area determination and a scaling factor. The scaling factor compensates for the lack of detail by assuming the product 106 in the likely product cluster counts of step 1136 are consistent with the average of the products 106 associated with the acceptable product boundaries of step 1130 and with the number of adjusted product boundaries resulting from step 1132. The scaling factor is therefore the quotient of the combined quantity of step 1138 divided by the summation of the acceptable product boundaries of step 1130 and with the number of adjusted product boundaries resulting from step 1132. This scaling factor will therefore be equal to or greater than 1. The scaled surface area determination is therefore the product of a surface area determination and the scaling factor. As provided above in connection with step 1154, the surface area determination is a function of the major axis length of step 1144 and the minor axis length of step 1144. While product-specific surface area equations have been determined for many types of products 106, for many products, the surface area determination can be obtained by assuming the product 106 is an ellipsoid. As the method 1100 does not obtain an actual thickness value, a scaled third axis length may be obtained by the product of the minor axis length of step 1144 and a product-specific scaling factor between 0.0 and 1.0. This scaling factor is known to be no greater than 1.0 as each product 106 settles to a stable position on the imaging table 114, which typically results in the smallest axis length being the thickness of the product. Because the general geometry of a product 106 is consistent within a type of product, regardless of the size of the product 106 within a group, the relationship between the length of a product's minor axis of step 1144 and the length of its third axis can be readily determined from materials known in the art or can be determined based on observation of a sample of product 106. As a result, the surface area determination is the sum of the ellipsoidal surface areas of each acceptable product boundary of step 1130 and each adjusted product boundary resulting from step 1132 using, for each, the length of its major axis, the length of its minor axis and the length of the scaled third axis.

In step 1162, the product count-per-weight is output to an information system, which may permit later further review of the product volume-per-weight of step 1154. As can be appreciated, method 1100 can be terminated after step 1160.

Figure 11E:
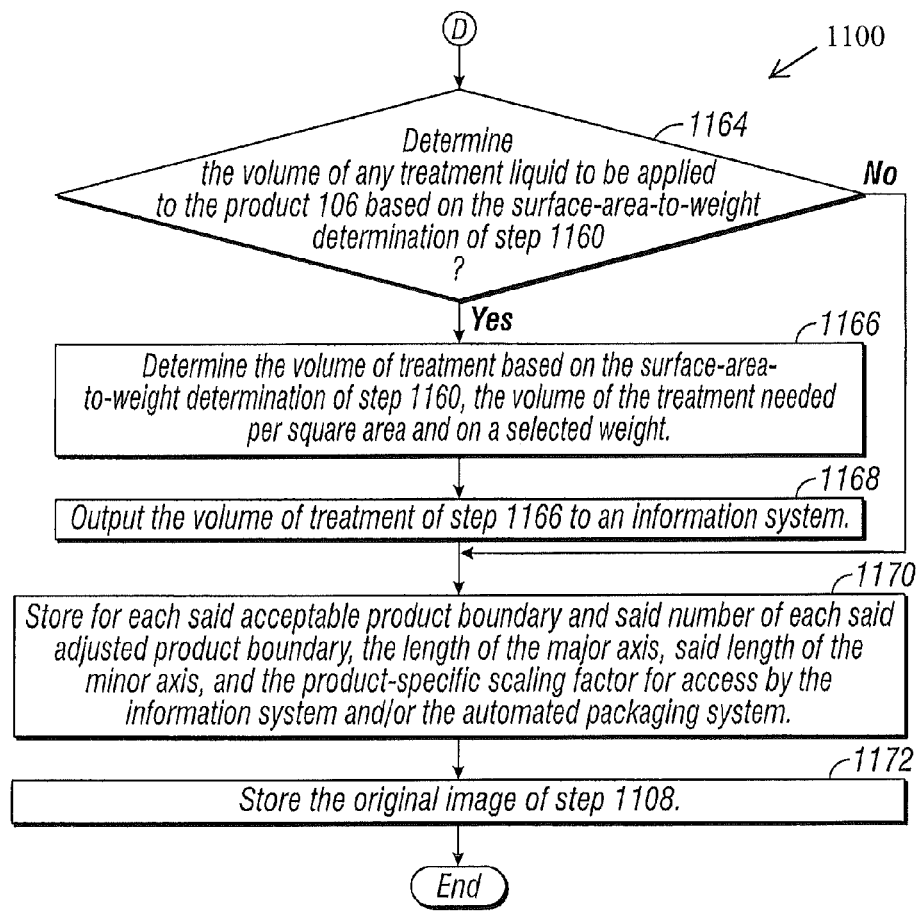
FIG. 11E is a continuation of the method illustrated in FIG. 11D.

The method 1100 continues to FIG. 11E. In step 1164, the method 1100 determines whether to determine the volume of any treatment liquid to be applied to the product 106 based on the surface-area-to-weight determination of step 1160. If no volume of any treatment liquid is to be determined, then the method 1100 proceeds to step 1164. If the volume of any treatment liquid is to be determined, then the method 1100 proceeds to step 1166.

In step 1166, the volume of treatment is determined based on the surface-area-to-weight determination of step 1160, the volume of the treatment needed per square area and on a selected weight. As can be appreciated, the determination can be driven by the desired weight, therefore driving the volume of treatment, or by a volume of treatment to be used, such as that filling the treatment container, therefore driving the weight of product 106 to be introduced.

In step 1168, the volume of treatment of step 1166 is output to an information system, which may permit later further review. As can be appreciated, method 1100 can be terminated after step 1168.

In step 1170, the method 1100 may store for each said acceptable product boundary and said number of each said adjusted product boundary, the length of the major axis, said length of the minor axis, and the product-specific scaling factor for access by the information system and/or the automated packaging system. As can be appreciated, method 1100 can be terminated after step 1170.

In step 1172, the method 1100 may store the original image. Method 1100 terminates after step 1172.

The terms and expressions which have been employed in the foregoing specification are used therein as terms of description and not of limitation, and there is no intention, in the use of such terms and expressions, of excluding equivalents of the features shown and described or portions thereof. It will be evident to those skilled in the art that various modifications and changes can be made thereto without departing from the broader spirit or scope of the disclosure. Accordingly, the specification is to be regarded in an illustrative rather than a restrictive sense. It is therefore, contemplated that various alternative embodiments and modifications may be made to the disclosed embodiments without departing from the spirit and scope of the disclosure defined by the appended claims and equivalents thereof.

We claim:
1. A method for determining characteristics for a plurality of preferred small fungible products in a volume of objects, comprising:
 defining an acceptable product size range and an average product size, said average product size having an average product size horizontal area;
 defining an acceptable morphologically eroded and dilated product area range;
 obtaining a monolayer sample of said volume;
 recording an original image, said first image including an image of said monolayer sample of said volume;
 generating a first alteration of the original image by morphologically eroding said original image until substantially all of said objects above said acceptable product size range appear separated;
 generating a second alteration of the original image by morphologically dilating said first alteration of the original image until nearly constituent with said original image, said second alteration of the original image containing a eroded-dilated image of each of said plurality of said preferred small fungible products;
  said second alteration of the original image composed of a plurality of pixels;
   each pixel of said plurality of pixels having an intensity within a first intensity range;
 identifying a preliminary boundary about each said eroded-dilated image of each of said plurality of said preferred small fungible products in said second alteration of the original image;
 generating a third alteration of the original image by altering said intensity of said each pixel of said plurality of pixels to an altered intensity within said first intensity range by
  increasing, within said first intensity range, said intensity of said each pixel of said plurality of pixels internal said preliminary boundary according to a distance from said preliminary boundary and
  decreasing, within said first intensity range, said intensity of said each pixel of said plurality of pixels external said preliminary boundary according to a distance from said preliminary boundary about each said eroded-dilated image to a minima;
 reducing said first intensity range to a second intensity range;
 generating a fourth alteration of the original image by reducing said altered intensity of said each pixel of said plurality of pixels in said third alteration of the original image to a reduced intensity of said each pixel of said plurality of pixels within said second intensity range;
 generating a fifth alteration of the original image by inverting said reduced intensity of said each pixel of said plurality of pixels within said second intensity range in said fifth alteration of the original image;
 defining a plurality of watershed boundaries in said fifth alteration of the original image by best fit connecting nearby said minima;
 generating a sixth alteration of the original image by reducing a variation of said inverted reduced intensity for said each pixel of said plurality of pixels in said fifth alteration of the original image between said each pixel of said plurality of pixels and an adjacent pixel of said plurality of pixels;
 identifying, using gradient analysis, an prospective product boundary for each said eroded-dilated image of each of said plurality of said preferred small fungible products found in said sixth alteration of the original image;

identifying as an acceptable product boundary each said prospective product boundary within said acceptable morphologically eroded and dilated product area range not bisected by any one of said plurality of watershed boundaries;

dividing any said prospective product boundary bisected by any one of said plurality of watershed boundaries into a first and a second adjusted product boundary along said any one of said plurality of watershed boundaries;

characterizing as a cluster each said prospective product boundary not identified as said acceptable product boundary and not divided into said first and a second adjusted product boundary, said cluster having a cluster horizontal area;

determining a likely cluster count for each said cluster by rounding to the nearest whole number a quotient of the division of said cluster horizontal area by said average product size horizontal area; and identifying a combined quantity of preferred small fungible products by the summation of a number of each said acceptable product boundary, a number of each said adjusted product boundary and a number of each said likely cluster count.

2. The method of claim 1, further comprising:

determining a sample weight of said monolayer sample on a scale;

identifying a major axis and a minor axis of each said acceptable product boundary and of each said adjusted product boundary;

determining a length of each said major axis and a length of each said minor axis for said each said acceptable product boundary and of each said adjusted product boundary; and determining one of a count-per-weight of said plurality of preferred small fungible products, a volume-per-weight of said plurality of preferred small fungible products, and a surface area-per-weight of said plurality of preferred small fungible products, wherein said count-per-weight being the quotient of said combined quantity divided by said sample weight;

wherein said volume-per-weight being the quotient of a scaled volume determination divided by said sample weight, said scaled volume determination being the product of a volume determination and a scaling factor, said scaling factor being the quotient of said combined quantity divided by a summation of said number of each said acceptable product boundary and said number of each said adjusted product boundary, said volume determination being a sum of an ellipsoidal volume of each of said acceptable product boundary and said adjusted product boundary, said ellipsoidal volume being a function of said length of said major axis, said length of said minor axis and a scaled third axis, said length of said third axis being the product of said length of said second axis and a product-specific scaling factor between 0.0 and 1.0; and wherein said surface area-per-weight being the quotient of a scaled surface area determination divided by said sample weight, said scaled surface area determination being the product of a surface area determination and a scaling factor, said scaling factor being the quotient of said combined quantity divided by a summation of said number of each said acceptable product boundary and said number of each said adjusted product boundary, said surface area determination being a sum of an ellipsoidal surface area of each of said acceptable product boundary and said adjusted product boundary, said ellipsoidal surface area being a function of said length of said major axis, said length of said minor axis and a scaled third axis, said length of said third axis being the product of said length of said second axis and a product-specific scaling factor between 0.0 and 1.0; and outputting said one of a count-per-weight, a volume-per-weight, and a surface area-per-weight to a information system.

3. The method of claim 2, further comprising:

storing, for each said acceptable product boundary and said number of each said adjusted product boundary, said length of said major axis, said length of said minor axis, and product-specific scaling factor for access by one of said information system and an automated packaging system.

4. The method of claim 1, further comprising:

storing said original image.

5. The method of claim 2, further comprising:

determining a volume of liquid product treatment for application to a weight of said product given said surface area-per-weight.

6. A method for determining characteristics for a plurality of preferred small fungible products in a volume of objects, comprising:

defining an average product size, said average product size having an average product size horizontal area;

obtaining a monolayer sample of said volume;

recording an original image, said first image including an image of said monolayer sample of said volume;

morphologically eroding, dilating, and adjusting said original image to obtain a plurality of preliminary boundaries in an altered image;

defining a plurality of watershed boundaries according to variations in said altered image external each said plurality of preliminary boundaries;

identifying as an acceptable product boundary each of said plurality of preliminary boundaries within said altered image not bisected by any one of said plurality of watershed boundaries;

dividing any said prospective product boundary bisected by any one of said plurality of watershed boundaries into a first and a second adjusted product boundary along said any one of said plurality of watershed boundaries;

characterizing as a cluster each said prospective product boundary not identified as said acceptable product boundary and not divided into said first and a second adjusted product boundary, said cluster having a cluster horizontal area;

determining a likely cluster count for each said cluster by rounding a quotient of the division of said cluster horizontal area by said average product size horizontal area;

identifying a combined quantity of preferred small fungible products by the summation of a number of each said acceptable product boundary, a number of each said adjusted product boundary and a number of each said likely cluster count;

determining a sample weight of said monolayer sample on a scale;

identifying a major axis and a minor axis of each said acceptable product boundary and of each said adjusted product boundary;

determining a length of each said major axis and a length of each said minor axis for said each said acceptable product boundary and of each said corrected adjusted product boundary; and determining one of a count-per-weight of said plurality of preferred small fungible products, a volume-per-weight of said plurality of preferred small fungible products, and a surface area-per-weight of said plurality of preferred small fungible products, wherein said count-per-weight being the quotient of said combined quantity divided by said sample weight;

wherein said volume-per-weight being the quotient of a scaled volume determination divided by said sample weight, said scaled volume determination being the product of a volume determination and a scaling factor, said scaling factor being the quotient of said combined quantity divided by a summation of said number of each said acceptable product boundary and said number of each said adjusted product boundary, said volume determination being a sum of a product-shape-specific volume of each of said acceptable product boundary and said adjusted product boundary, said product-shape-specific volume being a function of said length of said major axis, said length of said minor axis and a scaled third axis, said length of said third axis being the product of said length of said second axis and a product-specific scaling factor between 0.0 and 1.0; and wherein said surface area-per-weight being the quotient of a scaled surface area determination divided by said sample weight, said scaled surface area determination being the product of a surface area determination and a scaling factor, said scaling factor being the quotient of said combined quantity divided by a summation of said number of each said acceptable product boundary and said number of each said adjusted product boundary, said surface area determination being a sum of an product-shape-specific area of each of said acceptable product boundary and said adjusted product boundary, said product-shape-specific surface area being a function of said length of said major axis, said length of said minor axis and a length of a scaled third axis, said length of said third axis being the product of said length of said second axis and a product-specific scaling factor between 0.0 and 1.0; and outputting one of said one of a count-per-weight, a volume-per-weight, and a surface area-per-weight and, for each said acceptable product boundary and said number of each said adjusted product boundary, said length of said major axis, said length of said minor axis, and product-specific scaling factor.

7. A system for determining the product characteristics of preferable small fungible products within an acceptable size range, comprising:

an imaging table;

a camera, said camera adapted to transmit at least one image of said imaging table to a processor; and said processor adapted to perform the steps of:

defining an acceptable product size range and an average product size, said average product size having an average product size horizontal area;

defining an acceptable morphologically eroded and dilated product area range;

obtaining a monolayer sample of a volume of said preferable small fungible products within an acceptable size range;

recording an original image, said first image including an image of said monolayer sample of said volume;

generating a first alteration of the original image by morphologically eroding said original image until substantially all of said objects above said acceptable product size range appear separated;

generating a second alteration of the original image by morphologically dilating said first alteration of the original image until nearly constituent with said original image, said second alteration of the original image containing a eroded-dilated image of each of said plurality of said preferred small fungible products;

said second alteration of the original image composed of a plurality of pixels;

each pixel of said plurality of pixels having an intensity within a first intensity range;

identifying a preliminary boundary about each said eroded-dilated image of each of said plurality of said preferred small fungible products in said second alteration of the original image;

generating a third alteration of the original image by altering said intensity of said each pixel of said plurality of pixels to an altered intensity within said first intensity range by increasing, within said first intensity range, said intensity of said each pixel of said plurality of pixels internal said preliminary boundary according to a distance from said preliminary boundary and decreasing, within said first intensity range, said intensity of said each pixel of said plurality of pixels external said preliminary boundary according to a distance from said preliminary boundary about each said eroded-dilated image to a minima;

reducing said first intensity range to a second intensity range;

generating a fourth alteration of the original image by reducing said altered intensity of said each pixel of said plurality of pixels in said third alteration of the original image to a reduced intensity of said each pixel of said plurality of pixels within said second intensity range;

generating a fifth alteration of the original image by inverting said reduced intensity of said each pixel of said plurality of pixels within said second intensity range in said fifth alteration of the original image;

defining a plurality of watershed boundaries in said fifth alteration of the original image by best fit connecting nearby said minima;

generating a sixth alteration of the original image by reducing a variation of said inverted reduced intensity for said each pixel of said plurality of pixels in said fifth alteration of the original image between said each pixel of said plurality of pixels and an adjacent pixel of said plurality of pixels;

identifying, using gradient analysis, an prospective product boundary for each said eroded-dilated image of each of said plurality of said preferred small fungible products found in said sixth alteration of the original image;

identifying as an acceptable product boundary each said prospective product boundary within said acceptable morphologically eroded and dilated product area range not bisected by any one of said plurality of watershed boundaries;

dividing any said prospective product boundary bisected by any one of said plurality of watershed boundaries into a first and a second adjusted product boundary along said any one of said plurality of watershed boundaries;

characterizing as a cluster each said prospective product boundary not identified as said acceptable product boundary and not divided into said first and a second adjusted product boundary, said cluster having a cluster horizontal area;

determining a likely cluster count for each said cluster by rounding to the nearest whole number a quotient of the division of said cluster horizontal area by said average product size horizontal area; and identifying a combined quantity of preferred small fungible products by the summation of a number of each said acceptable product boundary, a number of each said adjusted product boundary and a number of each said likely cluster count.

8. The system of claim 7, wherein said processor is further adapted to perform the steps of:

determining a sample weight of said monolayer sample on a scale;

identifying a major axis and a minor axis of each said acceptable product boundary and of each said adjusted product boundary;

determining a length of each said major axis and a length of each said minor axis for said each said acceptable product boundary and of each said adjusted product boundary; and determining one of a count-per-weight of said plurality of preferred small fungible products, a volume-per-weight of said plurality of preferred small fungible products, and a surface area-per-weight of said plurality of preferred small fungible products, wherein said count-per-weight being the quotient of said combined quantity divided by said sample weight;

wherein said volume-per-weight being the quotient of a scaled volume determination divided by said sample weight, said scaled volume determination being the product of a volume determination and a scaling factor, said scaling factor being the quotient of said combined quantity divided by a summation of said number of each said acceptable product boundary and said number of each said adjusted product boundary, said volume determination being a sum of an ellipsoidal volume of each of said acceptable product boundary and said adjusted product boundary, said ellipsoidal volume being a function of said length of said major axis, said length of said minor axis and a scaled third axis, said length of said third axis being the product of said length of said second axis and a product-specific scaling factor between 0.0 and 1.0; and wherein said surface area-per-weight being the quotient of a scaled surface area determination divided by said sample weight, said scaled surface area determination being the product of a surface area determination and a scaling factor, said scaling factor being the quotient of said combined quantity divided by a summation of said number of each said acceptable product boundary and said number of each said adjusted product boundary, said surface area determination being a sum of an ellipsoidal surface area of each of said acceptable product boundary and said adjusted product boundary, said ellipsoidal surface area being a function of said length of said major axis, said length of said minor axis and a scaled third axis, said length of said third axis being the product of said length of said second axis and a product-specific scaling factor between 0.0 and 1.0; and outputting said one of a count-per-weight, a volume-per-weight, and a surface area-per-weight to a information system.

9. The system of claim 8, wherein said processor is further adapted to perform the steps of:

storing, for each said acceptable product boundary and said number of each said adjusted product boundary, said length of said major axis, said length of said minor axis, and product-specific scaling factor for access by one of said information system and an automated packaging system.

10. The system of claim 7, wherein said processor is further adapted to perform the steps of:

storing said original image.

11. The system of claim 8, wherein said processor is further adapted to perform the steps of:

determining a volume of liquid product treatment for application to a weight of said product given said surface area-per-weight.

12. A method for obtaining a desired quantity of preferred small fungible products from a flow of mixed products, comprising:

defining an acceptable product size range and an average product size, said average product size having an average product size horizontal area;

defining an acceptable morphologically eroded and dilated product area range;

obtaining a monolayer sample of said volume;

recording an original image, said first image including an image of said monolayer sample of said volume;

determining a sample weight of said monolayer sample;

generating a first alteration of the original image by morphologically eroding said original image until substantially all of said objects above said acceptable product size range appear separated;

generating a second alteration of the original image by morphologically dilating said first alteration of the original image until nearly constituent with said original image, said second alteration of the original image containing a eroded-dilated image of each of said plurality of said preferred small fungible products;

said second alteration of the original image composed of a plurality of pixels;

each pixel of said plurality of pixels having an intensity within a first intensity range;

identifying a preliminary boundary about each said eroded-dilated image of each of said plurality of said preferred small fungible products in said second alteration of the original image;

generating a third alteration of the original image by altering said intensity of said each pixel of said plurality of pixels to an altered intensity within said first intensity range by increasing, within said first intensity range, said intensity of said each pixel of said plurality of pixels internal said preliminary boundary according to a distance from said preliminary boundary and decreasing, within said first intensity range, said intensity of said each pixel of said plurality of pixels external said preliminary boundary according to a distance from said preliminary boundary about each said eroded-dilated image to a minima;

reducing said first intensity range to a second intensity range;

generating a fourth alteration of the original image by reducing said altered intensity of said each pixel of said plurality of pixels in said third alteration of the original image to a reduced intensity of said each pixel of said plurality of pixels within said second intensity range;

generating a fifth alteration of the original image by inverting said reduced intensity of said each pixel of said plurality of pixels within said second intensity range in said fifth alteration of the original image;

defining a plurality of watershed boundaries in said fifth alteration of the original image by best fit connecting nearby said minima;

generating a sixth alteration of the original image by reducing a variation of said inverted reduced intensity for said each pixel of said plurality of pixels in said fifth alteration of the original image between said each pixel of said plurality of pixels and an adjacent pixel of said plurality of pixels;

identifying, using gradient analysis, an prospective product boundary for each said eroded-dilated image of each of said plurality of said preferred small fungible products found in said sixth alteration of the original image;

identifying as an acceptable product boundary each said prospective product boundary within said acceptable morphologically eroded and dilated product area range not bisected by any one of said plurality of watershed boundaries;

dividing any said prospective product boundary bisected by any one of said plurality of watershed boundaries into a first and a second adjusted product boundary along said any one of said plurality of watershed boundaries;

characterizing as a cluster each said prospective product boundary not identified as said acceptable product boundary and not divided into said first and a second adjusted product boundary, said cluster having a cluster horizontal area;

determining a likely cluster count for each said cluster by rounding to the nearest whole number a quotient of the division of said cluster horizontal area by said average product size horizontal area; and identifying a combined quantity of preferred small fungible products by the summation of a number of each said acceptable product boundary, a number of each said adjusted product boundary and a number of each said likely cluster count;

determining a count-per-weight of said plurality of preferred small fungible products, said count-per-weight being the quotient of said combined quantity divided by said sample weight;

determining the desired weight associated with the desired quantity by dividing said desired quantity by said count-per-weight;

activating a bagger associated with said flow of mixed products, said bagger transmitting an actual bag weight to said final processor, said final processor comparing said actual bag weight to said desired weight; and terminating operation of said bagger when said actual bag weight is equivalent to said desired weight.

\* \* \* \* \*